United States Patent
Baneyx et al.

(10) Patent No.: US 10,030,046 B2
(45) Date of Patent: Jul. 24, 2018

(54) AFFINITY TAGS AND PROCESSES FOR PURIFYING AND IMMOBILIZING PROTEINS USING SAME

(71) Applicant: UNIVERSITY OF WASHINGTON THROUGH ITS CENTER FOR COMMERCIALIZATION, Seattle, WA (US)

(72) Inventors: Francois C. Baneyx, Seattle, WA (US); Brandon L. Coyle, Seattle, WA (US)

(73) Assignee: University of Washington, Seattle, WA (US)

(*) Notice: Subject to any disclaimer, the term of this patent is extended or adjusted under 35 U.S.C. 154(b) by 21 days.

(21) Appl. No.: 14/904,029

(22) PCT Filed: Sep. 19, 2014

(86) PCT No.: PCT/US2014/056651
§ 371 (c)(1),
(2) Date: Jan. 8, 2016

(87) PCT Pub. No.: WO2015/042464
PCT Pub. Date: Mar. 26, 2015

(65) Prior Publication Data
US 2016/0159856 A1 Jun. 9, 2016

Related U.S. Application Data

(60) Provisional application No. 61/880,012, filed on Sep. 19, 2013.

(51) Int. Cl.
| | |
|---|---|
| *C07K 1/13* | (2006.01) |
| *C07K 1/22* | (2006.01) |
| *C07K 7/08* | (2006.01) |
| *C07K 16/00* | (2006.01) |
| *C07K 1/20* | (2006.01) |

(52) U.S. Cl.
CPC ............... *C07K 1/22* (2013.01); *C07K 7/08* (2013.01); *C07K 16/00* (2013.01); *C07K 1/20* (2013.01); *C07K 2319/20* (2013.01)

(58) Field of Classification Search
CPC ..................................................... C07K 1/13
See application file for complete search history.

(56) References Cited

U.S. PATENT DOCUMENTS

| | | |
|---|---|---|
| 7,960,312 B2 | 6/2011 | Kuroda et al. |
| 8,283,443 B2 | 10/2012 | Kuroda et al. |
| 2005/0233307 A1 | 10/2005 | Gee et al. |
| 2010/0298169 A1 | 11/2010 | Wessels et al. |
| 2011/0167520 A1* | 7/2011 | Corbin .................. C07K 14/24 800/298 |
| 2013/0115635 A1 | 5/2013 | Pardon et al. |

FOREIGN PATENT DOCUMENTS

| | | |
|---|---|---|
| WO | 2007115860 A1 | 10/2007 |
| WO | 2015042464 A1 | 3/2015 |

OTHER PUBLICATIONS

Fuchs et al. 2005; Polyarginine as a multifunctional fusion tag. Protein Science. 14: 1538-1544.*
Ghose et al. 2004; Preparative protein purification on underderivatized silica. Biotechnology and Bioengineering. 82: 413-423.*
Taniguchi et al. 2007; The Si-tag for immobilizing proteins on a silica surface. Biotechnology and Bioengineering. 96(6): 1023-1029.*
Zhao et al. 2008; Progress of engineered antibody-targeted molecular imaging for solid tumors (Review). Molecular Medicine Reports. 1: 131-134.*
Aerogel.org (accessed Feb. 2017) "Silica Aerogel (TMOS, Base-Catalyzed)," available online at: http://www.aerogel.org/?p=1406.
Abu-Elheiga, L. et al., (Mar. 2001). Continuous fatty acid oxidation and reduced fat storage in mice lacking acetyl-CoA carboxylase 2. Science 291, 2613-2616.
Adijanto, J. et al., (Sep. 2014). Cultured primary human fetal retinal pigment epithelium (hfRPE) as a model for evaluating RPE metabolism. Exp. Eye Res. 126, 77-84.
Arnau, J. et al., Current strategies for the use of affinity tags and tag removal for the purification of recombinant proteins, Protein Expression and Purification, 48(1):1-13 (Jul. 2006).
Arumugam, S. et al., Attach, Remove, or Replace: Reversible Surface Functionalization Using Thiol-Quinone Methide Photoclick Chemistry, J. Am. Chem. Soc., May 2012, 134, 8408-8411.
Astashkina, A. et al., (Apr. 2012). A critical evaluation of in vitro cell culture models for high-throughput drug screening and toxicity. Pharmacology & Therapeutics 134, 82-106.
Baneyx, F. et al., In vivo degradation of secreted fusion proteins by the *Escherichia coli* outer membrane protein OmpT, J. Bacteriol., 172(1):491-494 (Jan. 1990).
Baneyx, F., Recombinant Protein Expression in *Escherichia coli*. Curr. Opin. Biotechnol., Oct. 1999, 10, 411-421.
Baneyx, F. et al., Selection and Analysis of Solid-Binding Peptides. Curr. Opin. Biotechnol., Aug. 2007, 18, 312-317.
Baur, J.A. et al., (Aug. 2014). Control of gluconeogenesis by metformin: does redox trump energy charge? Cell Metab. 20, 197-199.
Bernard, Andre et al., (epub Apr. 1998) "Printing Patterns of Proteins," Langmuir, 14(9):2225-2229.
Bernard, Andre et al., (Jul. 2000) "Microcontact Printing of Proteins," Advanced Materials, 12(14):1067-1070.
Boul, P. et al., Reversible Sidewall Functionalization of Buckytubes. Chem. Phys. Lett., Sep. 1999, 310, 367-372.

(Continued)

*Primary Examiner* — Karen Cochrane Carlson
(74) *Attorney, Agent, or Firm* — Perkins Coie LLP

(57) ABSTRACT

The present disclosure provides affinity tags, fusion proteins comprising one or more affinity tags, compositions comprising a fusion protein, methods of purifying a protein using an affinity tag, and devices for purifying a protein using an affinity tag.

15 Claims, 13 Drawing Sheets

(56) References Cited

OTHER PUBLICATIONS

Braden, B.C. et al., X-ray Crystal Structure of an Anti-Buckminsterfullerene Antibody Fab Fragment: Biomolecular Recognition of C(60). Proc. Natl. Acad. Sci. U.S.A., Oct. 2000, 97, 12193-12197.
Braunschweig, A.B. et al., Molecular Printing, Nat. Chem., Aug. 2009, 1, 353-358.
Buckley, A.M. et al., The sol-gel preparation of silica gels, J Chem Educ, 71(7):599-602 (Jul. 1994).
Buhl, M. et al., Immobilization of enzymes via microcontact printing and thiol-ene click chemistry, Bioconjugate Chem., Jun. 2015, 26, 1017-1020.
Burghardt, T.P. et al., Total Internal Reflection/Fluorescence Photobleaching Recovery Study of Serum Albumin Adsorption Dynamics. Biophys. J., Mar. 1981, 33, 455-467.
Butler, J.E. et al., Solid supports in enzyme-linked immunosorbent assay and other solid-phase immunoassays, Methods, Sep. 2000, 22, 4-23.
Care, A. et al., Solid-binding peptides: smart tools for nanobiotechnology, Trends Biotechnol., May 2015, 33, 259-268.
Chan, W.C.W. et al., Quantum Dot Bioconjugates for Ultrasensitive Nonisotopic Detection. Science, Sep. 1998, 281, 2016-2018.
Chen, C.L. et al., Peptide-based methods for the preparation of nanostructured inorganic materials, Angew. Chem. Int. Ed., Mar. 2010, 49, 1924-1942.
Chiu, D. et al., Biomineralization and size control of calcium phosphate core-protein shell nanoparticles: potential for vaccine applications, Bioconjug. Chem., 23(3):610-617 (Mar. 2012).
Choe, W.S. et al., Conformational control of inorganic adhesion in a designer protein engineered for cuprous oxide binding, Langmuir, 23(23):11347-11350 (Nov. 2007).
Cormack, B.P. et al., FACS-optimized mutants of the green fluorescent protein (GFP), Gene, 173(1 Spec No.):33-38 (1996; retrieved Aug. 2016).
Coyle, B.L. et al., (epub May 2016) "Direct and Reversible Immobilization and Microcontact Printing of Functional Proteins Using a Genetically Appended Silica-Binding Tag," Chemical Communications, 52(43):7001-7004.
Coyle, B.L. et al., (Jan. 2013) "Protein-aided mineralization of inorganic nanostructures," In: Rehm BHA, editor. Bionanotechnology: Biological self-assembly and its applications. Norwich, UK: Caister Academic Press, pp. 63-84.
Coyle, B.L. et al., (Oct. 2014) "A cleavable silica-binding affinity tag for rapid and inexpensive protein purification," Biotechnology and Bioengineering, 111(10):2019-2026.
Cui, Y. et al., Chemical Functionalization of Graphene Enabled by Phage Displayed Peptides. Nano Lett., Nov. 2010, 10, 4559-4565.
Dai, H. et al., Nonequilibrium Synthesis and Assembly of Hybrid Inorganic-Protein Nanostructures Using an Engineered DNA Binding Protein. J. Am. Chem. Soc., Nov. 2005, 127, 15637-15643.
Davis, E.J. et al., (Sep. 1980). Pyruvate carboxylase and propionyl-CoA carboxylase as anaplerotic enzymes in skeletal muscle mitochondria. Eur. J. Biochem. 110, 255-262.
Delamarche, E. et al., Microcontact printing of proteins. In Nanobiotechnology, Niemeyer, C. M.; Mirkin, C. A., Eds. WileyVCH: Weinheim, pp. 31-52, 2004; retrieved Feb. 2017.
Dell'Aglio, D.M. et al., (Dec. 2009). Acute metformin overdose: examining serum pH, lactate level, and metformin concentrations in survivors versus nonsurvivors: a systematic review of the literature. Ann. Emerg. Med. 54, 818-823.
Deng, X. et al., Bio-orthogonal "double-click" chemistry based on multifunctional coatings, Angew. Chem. Int. Ed., Jul. 2011, 50, 6522-6526.
Dias, A.O. et al., Recent advances in bioprinting and applications for biosensing, Biosensors (Basel), Apr. 2014, 4, 111-136.
Dickerson, M.B. et al., Protein- and Peptide Directed Synthesis of Inorganic Materials. Chem. Rev., Nov. 2008, 108, 4935-4978.
Dieckmann, G.R. et al., Controlled Assembly of Carbon Nanotubes by Designed Amphiphilic Peptide Helices. J. Am. Chem. Soc., Feb. 2003, 125, 1770-1777.

Diepart, C. et al., (Jan. 2010). Comparison of methods for measuring oxygen consumption in tumor cells in vitro. Anal. Biochem. 396, 250-256.
Du, J. et al., (Dec. 2013). Inhibition of mitochondrial pyruvate transport by zaprinast causes massive accumulation of aspartate at the expense of glutamate in the retina. J. Biol. Chem. 288, 36129-36140.
Ehmann, U.K. et al., (Oct. 1983). $CO_2$/bicarbonate stimulates growth independently of PH in mouse mammary epithelial cells. In vitro 19, 767-774.
Ekblad, T. et al., Protein adsorption and surface patterning, Curr. Opin. Colloid Interface Sci., Dec. 2010, 15, 499-509.
El-Mir, M.Y. et al., (Jan. 2000) Dimethylbiguanide inhibits cell respiration via an indirect effect targeted on the respiratory chain complex I. J Biol Chem 275, 223-228.
Erathodiyil, N. et al., Functionalization of inorganic nanoparticles for biomiaging applications, Acc Chem Res, 44(10):925-935 (Oct. 2011).
Ferrari, A.C. et al., Raman Spectroscopy of Amorphous, Nanostructured, Diamond-Like Carbon, and Nanodiamond. Philos. Trans. A, Nov. 2004, 362, 2477-2512.
Ganesan, R. et al., Multicomponent protein patterning of material surfaces. J. Mater. Chem., epub Jul. 2010, 20, 7322-7331.
Gayda, R.C. et al., (Oct. 1978) Cloned DNA fragment specifying major outer membrane protein a in *Escherichia coli* K-12. J Bacteriol 136(1):369-380.
Geim, A.K. et al., Graphene: Status and Prospects. Science, Jun. 2009, 324, 1530-1534.
Gerencser, A.A. et al., (Aug. 2009). Quantitative microplate-based respirometry with correction for oxygen diffusion. Anal. Chem. 81, 6868-6878.
Ghose, S. et al., (Aug. 2004) Preparative protein purification on underivatized silica. Biotechnol Bioeng 87(3):413-423.
Gray, J.J. , The interaction of proteins with solid surfaces, Curr. Opin. Struct. Biol., Feb. 2004, 14, 110-115.
Grodberg, J. et al., (Mar. 1988) ompT encodes the *Escherichia coli* outer membrane protease that cleaves T7 RNA polymerase during purification. J Bacteriol 170(3):1245-1253.
Grosh, C. et al., Protein-Based Control of Silver Growth Habit Using Electrochemical Deposition. Cryst. Growth Des., epub Aug. 2009, 9, 4401-4406.
Grunwald, C. et al., In Situ Assembly of Macromolecular Complexes Triggered by Light, Proc. Natl. Acad. Sci. U. S. A., Apr. 2010, 107, 6146-6151.
Guo, S., Graphene Nanosheet: Synthesis, Molecular Engineering, Thin Film, Hybrids, and Energy and Analytical Applications. Chem. Soc. Rev., May 2011, 40, 2644-2672.
Haensch, C. et al., Chemical modification of self-assembled silane based monolayers by surface reactions, Chem Soc Rev, 39(6):2323-2334 (Jun. 2010).
Han, C.Y. et al., (Mar. 2012). NADPH oxidase-derived reactive oxygen species increases expression of monocyte chemotactic factor genes in cultured adipocytes. J. Biol. Chem. 287, 10379-10393.
Harris, P.J.F. , Fullerene-Related Structure of Commercial Glassy Carbons. Philos. Mag., 2004, epub. Aug. 2006, 84, 3159-3167.
Henquin, J.C. et al., (Feb. 1975). Extracellular bicarbonate ions and insulin secretion. Biochim. Biophys. Acta 381, 437-442.
Henquin, J.C. et al., (Sep. 1976). Bicarbonate modulation of glucose-induced biphasic insulin release by rat islets. Am. J. Physiol. 231, 713-721.
Hnilova, M. et al., Effect of molecular conformations on the adsorption behavior of gold-binding peptides, Langmuir, 24(21):12440-12445 (Nov. 2008).
Holmgren, A. , Thioredoxin. Annu. Rev. Biochem., Jul. 1985, 54, 237-271.
Homola, J., Surface Plasmon Resonance Sensors for Detection of Chemical and Biological Species. Chem. Rev., Feb. 2008, 108, 462-493.
Hritonenko, V. et al., Omptin proteins: an expanding family of outer membrane proteases in gram-negative Enterobacteriaceae, Mol Membr Biol, 24(5-6):395-406 (Sep.-Dec. 2007).
Huo, F. et al., Polymer pen lithography, Science, Sep. 2008, 321, 1658-1660.

(56) References Cited

OTHER PUBLICATIONS

Jacobus, W.E. et al., (Mar. 1982). Mitochondrial respiratory control. Evidence against the regulation of respiration by extramitochondrial phosphorylation potentials or by [ATP]/[ADP] ratios. J. Biol. Chem. 257, 2397-2402.

Kacar, T. et al., Directed self-immobilization of alkaline phosphatase on micro-patterned substrates via genetically fused metal-binding peptide, Biotechnol. Bioeng., Jul. 2009, 103, 696-705.

Kacar, T. et al., Quartz Binding Peptides as Molecular Linkers towards Fabricating Multifunctional Micropatterned Substrates, Adv. Mater., Jan. 2009, 21, 295-299.

Kase, D. et al., Affinity Selection of Peptide Phage Libraries against Single-Wall Carbon Nanohorns Identifies a Peptide Aptamer with Conformational Variability. Langmuir, Sep. 2004, 20, 8939-8941.

Kattie, S.K. et al., Crystal Structure of Thioredoxin from *Escherichia coli* at 1.68 Å Resolution. J. Mol. Biol., Mar. 1990, 212, 167-184.

Kim, S.N. et al., Preferential Binding of Peptides to Graphene Edges and Planes. J. Am. Chem. Soc., Sep. 2011, 133, 14480-14483.

Kitayaporn, S. et al., Laying out Ground Rules for Protein-Aided Nanofabrication: ZnO Synthesis at 70° C. as a Case Study. Biotechnol. Bioeng., Aug. 2012, 109, 1912-1918.

Kolawole, J.A. et al., (Jul.-Sep. 2002). Chronopharmacokinetics of acetaminophen in healthy human volunteers. Eur. J. DrugMetab. Pharmacokinet. 27, 199-202.

Kumar, A. et al., Features of gold having micrometer to centimeter dimensions can be formed through a combination of stamping with an elastomeric stamp and an alkanethiol "ink" followed by chemical etching. Appl. Phys. Lett., Oct. 1993, 63, 2002-2004.

Kunzelmann, U. et al., Biosensor properties of glucose oxidase immobilized within SiO2 gels, Sensor Actuat B, 38-39(1-3):222-228 (Mar.-Apr. 1997).

Kuo, W.H. et al., Exploiting the interactions between poly-histidine fusion tags and immobilized metal ions, Biotechnol Lett, 33(6):1075-1084 (Jun. 2011).

Kyte, J. et al., A Simple Method for Displaying the Hydropathic Character of a Protein. J. Mol. Biol., May 1982, 157, 105-132.

Lavallie, E.R. et al., Thioredoxin as a Fusion Partner for Production of Soluble Recombinant Proteins in *Escherichia coli*. Methods Enzymol., 2000; retrieved Aug. 2016, 326, 322-340.

Lee, S. et al., Synthesis and Application of Virus-Based Hybrid Nanomaterials. Biotechnol. Bioeng., Jan. 2012, 109, 16-30.

Lee, W.M., (Feb. 2012). Acute liver failure. Semin. Respir. Crit. Care Med. 33, 36-45.

Lichty, J.J. et al., Comparison of affinity tags for protein purification, Protein Expression and Purification, 41(1):98-105 (May 2005).

Liu, Z. et al., Carbon Nanotubes in Biology and Medicine: In Vitro and in Vivo Detection, Imaging and Drug Delivery. Nano Res, Feb. 2009, 2, 85-120.

Lu, Z. et al., Expression of thioredoxin random peptide libraries on the *Escherichia coli* cell surface as functional fusions to flagellin: a system designed for exploring protein-protein interactions, Nature Biotechnology, 13(4):366-372 (Apr. 1995).

Lunn, C.A. et al., Localization of Thioredoxin from *Escherichia coli* in an Osmotically Sensitive Compartment. J. Biol. Chem., Oct. 1982, 257, 11424-11430.

Madiraju, A.K. et al., (Jun. 2014). Metformin suppresses gluconeogenesis by inhibiting mitochondrial glycerophosphate dehydrogenase. Nature 510, 542-546.

Malan, J. et al., (Jun. 1985). Chronopharmacokinetics of paracetamol in normal subjects. Br. J. Clin. Pharmacol. 19, 843-845.

Manoil, C. et al., Insertion of In-Frame Sequence Tags into Proteins Using Transposons, Methods, Jan. 2000, 20, 55-61.

Mathe, C. et al., Structural determinants for protein adsorption/non-adsorption to silica surface, PLoS One, Nov. 2013, 8, e81346.

McKim, J.M., (Feb. 2010) Building a tiered approach to in vitro predictive toxicity screening: a focus on assays with in vivo relevance. Combinatorial chemistry & high throughput screening 13, 188-206.

Mitaka, T. et al., (Jul. 1991). The bicarbonate ion is essential for efficient DNA synthesis by primary cultured rat hepatocytes. In vitro Cell. Dev. Biol J. Tissue Culture Assoc. 27A, 549-556.

Nannenga, B.L. et al., Reprogramming chaperone pathways to improve membrane protein expression in *Escherichia coli*, Protein Sci, 20(8):1411-1420 (Aug. 2011).

Neal, A. et al., (Dec. 2015) "Quantification of Low-Level Drug Effects Using Real-Time, in vitro Measurement of Oxygen Consumption Rate," Toxicological Sciences, 148(2):594-602.

Nieba, L. et al., BIACORE analysis of histidine-tagged proteins using a chelating NTA sensor chip, Anal Biochem, 252(2):217-228 (Oct. 1997).

Nossal, N.G. et al., The Release of Enzymes by Osmotic Shock from *Escherichia coli* in Exponential Phase. J. Biol. Chem., Jul. 1966, 241, 3055-3062.

O'Brien, P.J. et al., (Jul. 2014). High-content analysis in toxicology: screening substances for human toxicity potential, elucidating subcellular mechanisms and in vivo use as translational safety biomarkers. Basic Clin. Pharmacol. Toxicol. 115, 4-17.

Oh, D. et al., Graphene Sheets Stabilized on Genetically Engineered M13 Viral Templates as Conducting Frameworks for Hybrid Energy-Storage Materials. Small, Apr. 2012, 8, 1006-1011.

Ortiz-Acevedo, A. et al., Diameter-Selective Solubilization of Single-Walled Carbon Nanotubes by Reversible Cyclic Peptides. J. Am. Chem. Soc., Jul. 2005, 127, 9512-9517.

Park, T.J. et al., Protein nanopatterns and biosensors using gold binding polypeptide as a fusion partner, Anal. Chem., Oct. 2006, 78, 7197-7205.

Parrish, A.R. et al., (1995; retrieved Aug. 2016). Precision-cut tissue slices: applications in pharmacology and toxicology. Life Sci. 57, 1887-1901.

Patwardhan, S.V. et al., (Apr. 2012) Chemistry of aqueous silica nanoparticle surfaces and the mechanism of selective peptide adsorption. J Am Chem Soc 134(14):6244-6256.

Pedelacq, J.D. et al., Engineering and Characterization of a Superfolder Green Fluorescent Protein, Nat. Biotechnol., Jan. 2006, 24, 79-88.

Quist, A.P. et al., Recent advances in microcontact printing. Anal. Bioanal. Chem., Feb. 2005, 381, 591-600.

Qureshi, A. et al., Review on Carbon-Derived, Solid-State, Micro and Nano Sensors for Electrochemical Sensing Applications. Diamond Relat. Mater., Dec. 2009, 18, 1401-1420.

Reigner, B.G. et al., (Feb. 2002) Estimating the starting dose for entry into humans: principles and practice. European journal of clinical pharmacology 57, 835-845.

Robertson, J. , Diamond-Like Amorphous Carbon. Mater. Sc. Eng., R, May 2002, 37, 129-281.

Ruiz, S.A. et al., Microcontact printing: A tool to pattern. Soft Matter, 2007; epub Dec. 2006, 3, 168-177.

Sahni, J. et al., (Sep. 2010). TRPM7 regulates quiescent/proliferative metabolic transitions in lymphocytes. Cell Cycle 9, 3565-3574.

Sarikaya, M. et al., Materials Assembly and Formation Using Engineered Polypeptides. Annu. Rev. Mater. Res., Aug. 2004, 34, 373-408.

Schickinger, S. et al., (Dec. 2013). Nanosecond ratio imaging of redox states in tumor cell spheroids using light sheet-based fluorescence microscopy. J. Biomed. Optics 18, 126007.

Schoonen, W.G. et al., (2009; retrieved Aug. 2016). High-throughput screening for analysis of in vitro toxicity. EXS 99, 401-452.

Schoonen, W.G. et al., (Apr. 2012). Cytotoxic effects of 109 reference compounds on rat H4IIE and human HepG2 hepatocytes. III: Mechanistic assays on oxygen consumption with MitoXpress and NAD(P)H production with Alamar Blue. Toxicol. In Vitro 26, 511-525.

Sedlak, R.H. et al., Engineered *Escherichia coli* Silver-Binding Periplasmic Protein That Promotes Silver Tolerance. Appl. Environ. Microbiol., Apr. 2012, 78, 2289-2296.

Seker, U.O.S. et al., Adsorption behavior of linear and cyclic genetically engineered platinum binding peptides, Langmuir, 23(15):7895-7900 (Jul. 2007).

Seker, U.O.S. et al., Material Binding Peptides for Nanotechnology. Molecules, Feb. 2011, 16, 1426-1451.

(56) References Cited

OTHER PUBLICATIONS

Sengupta, A. et al., A Genetic Approach for Controlling the Binding and Orientation of Proteins on Nanoparticles. Langmuir, Mar. 2008, 24, 2000-2008.
Shen, H. et al., Biomedical Applications of Graphene. Theranostics, Mar. 2012, 2, 283-294.
Silva, F.M. et al., (Jul. 2010). Effects of metformin on glucose metabolism of perfused rat livers. Mol Cell Biochem. 340, 283-289.
So, C.R. et al., Controlling Self-Assembly of Engineered Peptides on Graphite by Rational Mutation. ACS Nano, Feb. 2012, 6, 1648-1656.
Soto, C.M. et al., Virus Hybrids as Nanomaterials for Biotechnology. Curr. Opin. Biotechnol., Aug. 2010, 21, 426-438.
Stangier, J. et al., (Dec. 2000). Pharmacokinetics of acetaminophen and ibuprofen when coadministered with telmisartan in healthy volunteers. J. Clin. Pharmacol. 40, 1338-1346.
Still, W.C., (Jul. 1978) Rapid chromatography technique for preparative separations with moderate resolution. J Org Chem 43:2923-2925.
Strauch, K.M. et al., (May 1989) Characterization of degP, a gene required for proteolysis in the cell envelope and essential for growth of *Escherichia coli* at high temperature. J Bacteriol 171:2689-2696.
Stutz, H. et al., (Jun. 2009) Protein attachment on silica surfaces—A survey of molecular fundamentals, resulting effects and novel preventive strategies in CE. Electrophoresis 30:2032-2061.
Su, Z. et al., Single-Walled Carbon Nanotube Binding Peptides: Probing Tryptophan's Importance by Unnatural Amino Acid Substitution. J. Phys. Chem. B, Dec. 2007, 111, 14411-14417.
Sugimura, K. et al., (Dec. 1988) Purification, characterization, and primary structure of *Escherichia coli* protease VII with specificity for paired basic residues: Identity of protease VII and OmpT. J Bacteriol 170:5625-5632.
Sweet, I.R. et al., (2002; epub Jul. 2004) Continuous measurement of oxygen consumption by pancreatic islets. Diabetes Technol Ther 4, 661-672.
Sweet, I.R. et al., (2002; epub Jul. 2004) Dynamic perifusion to maintain and assess isolated pancreatic islets. Diabetes Technol Ther 4, 67-76.
Sweet, I.R. et al., (Dec. 2006). Contribution of calcium influx in mediating glucose-stimulated oxygen consumption in pancreatic islets. Diabetes 55, 3509-3519.
Sweet, I.R. et al., (Jan. 2008). Glucose-stimulated increment in oxygen consumption rate as a standardized test of human islet quality. Am. J. Transplant. 8, 183-192.
Sweet, I.R. et al., (Oct. 2005). Glucose stimulation of cytochrome C reduction and oxygen consumption as assessment of human islet quality. Transplantation 80, 1003-1011.
Tamerler, C. et al., Molecular biomimetics: GEPI-based biological routes to technology, Biopolymers, Jan. 2010, 94, 78-94.
Taniguchi, K. et al., (Apr. 2007) "The Si-tag for immobilizing proteins on a silica surface," Biotechnology and Bioengineering, 96(6):1023-1029.
Thai, C.K. et al., Identification and Characterization of Cu2O- and ZnOBinding Polypeptides by *Escherichia coli* Cell Surface Display: Toward an Understanding of Metal Oxide Binding. Biotechnol. Bioeng., Jul. 2004, 87, 129-137.
Thedinga, E. et al., (2007; retrieved Aug. 2016). In vitro system for the prediction of hepatotoxic effects in primary hepatocytes. Altex 24, 22-34.
Thomas, J.G. et al., (May 1996) Protein misfolding and inclusion body formation in recombinant *Escherichia coli* cells overproducing heat-shock proteins. J Biol Chem 271:11141-11147.
Tolstyka, Z.P. et al., Chemoselective immobilization of proteins by microcontact printing and bio-orthogonal click reactions, ChemBioChem, Dec. 2013, 14, 2464-2471.
Tomasio, S.M. et al., Modeling the Binding Affinity of Peptides for Graphitic Surfaces. Influence of Aromatic Content and Interfacial Shape. J. Phys. Chem. C, epub Apr. 2009, 113, 8778-8785.
Utter, M.F. et al., (May 1960). Formation of oxaloacetate from pyruvate and carbon dioxide. J. Biol. Chem. 235, PC17-PC18.
Vickers, A.E. et al., (Oct. 2011). Repair pathways evident in human liver organ slices. Toxicol. In Vitro 25, 1485-1492.
Vigolo, B. et al., Macroscopic Fibers and Ribbons of Oriented Carbon Nanotubes. Science, Nov. 2000, 290, 1331-1334.
Voskuhl, J. et al., Advances in contact printing technologies of carbohydrate, peptide and protein arrays. Curr. Opin. Chem. Biol., Feb. 2014, 18, 1-7.
Voskuhl, J. et al., Immobilization of liposomes and vesicles on patterned surfaces by a peptide coiled-coil binding motif, Angew. Chem. Int. Ed., Dec. 2012, 51, 12616-12620.
Wan, P. et al., Fabrication of Reactivated Biointerface for Dual-Controlled Reversible Immobilization of Cytochrome C, Adv. Mater., Nov. 2009, 21, 4362-4365.
Wang, R. et al., (2015; epub Nov. 2014). The acute extracellular flux (XF) assay to assess compound effects on mitochondrial function. J. Biomol. Screen 20, 422-429.
Wang, S. et al., Peptides with Selective Affinity for Carbon Nanotubes. Nat. Mater., Mar. 2003, 2, 196-200.
Wang, Y. et al., Graphene and Graphene Oxide: Biofunctionalization and Applictions in Biotechnology. Trends Biotechnol., May 2011, 29, 205-212.
Wasserberg, D. et al., Oriented protein immobilization using covalent and noncovalent chemistry on a thiol-reactive self-reporting surface, J. Am. Chem. Soc., Feb. 2013, 135, 3104-3111.
Waugh, D.S. et al., An overview of enzymatic reagents for the removal of affinity tags, Protein expression and purification, 80(2):283-293 (Dec. 2011).
Wendeln, C. et al., Rapid preparation of multifunctional surfaces for orthogonal ligation by microcontact chemistry, Chemistry, May 2012, 18, 5880-5888.
Wendeln, C. et al., Surface patterning by microcontact chemistry. Langmuir, Apr. 2012, 28, 5527-5538.
Wessel, D. et al., (Apr. 1984) A method for the quantitative recovery of protein in dilute solution in the presence of detergents and lipids. Anal Biochem. 138:141-143.
Weydt, P. et al., (Nov. 2006). Thermoregulatory and metabolic defects in Huntington's disease transgenic mice implicate PGC-1alpha in Huntington's disease neurodegeneration. Cell Metab. 4, 349-362.
Wills, L.P. et al., (Oct. 2013). Highthroughput respirometric assay identifies predictive toxicophore of mitochondrial injury. Toxicol. Appl. Pharmacol. 272, 490-502.
Wolf, P. et al., (Dec. 2013). Automated platform for sensor-based monitoring and controlled assays of living cells and tissues. Biosensors Bioelectron. 50, 111-117.
Wu, J. et al., Graphenes as Potential Material for Electronics. Chem. Rev., Mar. 2007, 107, 718-747.
Xia, Y.N.W. et al., Soft Lithography. Annu Rev Mat Sci, Aug. 1998, 28, 153-184.
Xie, H. et al., Ranking the Affinity of Aromatic Residues for Carbon Nanotubes by Using Designed Surfactant Peptides. J. Pept. Sci., Feb. 2008, 14, 139-151.
Xu, H. et al., Versatile stamps in microcontact printing: transferring inks by molecular recognition and from ink reservoirs. Chemistry, Feb. 2010, 16, 2342-2348.
Yang, D.Q. et al., Interaction of Evaporated Nickel Nanoparticles with Highly Oriented Pyrolytic Graphite: Back-Bonding to Surface Defects, as Studied by X-ray Photoelectron Spectroscopy. J. Phys. Chem. B, Oct. 2005, 109, 19329-19334.
Yang, L. et al., Reversible and oriented immobilization of ferrocene-modified proteins, J. Am. Chem. Soc., Nov. 2012, 134, 19199-19206.
Yano, Y.F., Kinetics of protein unfolding at interfaces, J. Phys.: Condens. Matter, Dec. 2012, 24, 503101.
Young, J.F. et al., Strong and Reversible Monovalent Supramolecular Protein Immobilization, ChemBioChem, Jan. 2010, 11, 180-183.
Yu, T. et al., Recognition of Carbon Nanotube Chirality by Phage Display. RSC Adv., epub Dec. 2011, 2, 1466-1476.
Zemmel, R. et al., (2010; accessed Aug. 2016) McKinsey & Company. Invention reinvented: McKinsey perspectives on pharmaceutical R & D.

(56) References Cited

OTHER PUBLICATIONS

Zhou, W. et al., Single Pot Biofabrication of Zinc Sulfide Immuno-Quantum Dots. J. Am. Chem. Soc., Apr. 2010, 132, 4731-4738.

Zorbas, V. et al., Importance of Aromatic Content for Peptide/Single Wall Carbon Nanotube Interactions. J. Am. Chem. Soc., Sep. 2005, 127, 12323-12328.

Chen, H.B. et al., Context-dependent adsorption behavior of cyclic and linear peptides on metal oxide, Langmuir, 25(3):1588-1593 (Feb. 2009).

Shaner, N.C. et al., Improved monomeric red, orange and yellow fluorescent proteins derived from *Discosoma* sp. red fluorescent protein, Nat Biotechnol, 22(12):1567-1572 (Dec. 2004).

Sweet, I. R., et al. (Feb. 2004). Regulation of ATP/ADP in pancreatic islets. Diabetes 53, 401-409.

Sarikaya, M. et al., Molecular Biomimetics: Nanotechnology through Biology. Nat. Mater., Sep. 2003, 2, 577-585.

Hyun, J. et al., Capture and Release of Proteins on the Nanoscale by Stimuli-Responsive Elastin-Like Polypeptide "Switches", J. Am. Chem. Soc., Jun. 2004, 126, 7330-7335.

International Search Report and Written Opinion dated Dec. 3, 2014 in International Application No. PCT/US2014/056651, 11 pages.

Coyle, et al., "Carbon-binding designer proteins that discriminate between sp2- and sp3-hybridized carbon surfaces", Langmuir, Apr. 2, 2013, pp. 4839-4846.

Ikeda, et al., "Single-step affinity purification of recombinant proteins using the silica-binding Si-tag as a fusion partner", Protein Expr Purif., Dec. 23, 2009, pp. 91-95.

Massari, et al., "Dynamics of proteins encapsulated in silica sol-gel glasses studied with IR vibrational echo spectroscopy", J Am Chem Soc., Mar. 29, 2006, pp. 990-399.7.

\* cited by examiner

AFFINITY TAGS AND PROCESSES FOR PURIFYING AND IMMOBILIZING PROTEINS USING SAME

CROSS-REFERENCE TO RELATED APPLICATIONS

This application claims the benefit of U.S. Provisional Patent Application No. 61/880,012, filed Sep. 19, 2013, the entire contents of which is incorporated herein by reference.

STATEMENT REGARDING FEDERALLY FUNDED RESEARCH

This invention was made with government support under grant no. DMR-0520567, awarded by the National Science Foundation, and grant no. N00014-12-1-1013, awarded by the Office of Naval Research. The government has certain rights in the invention.

TECHNICAL FIELD

The present disclosure relates to affinity tags, fusion proteins comprising one or more affinity tags, compositions comprising a fusion protein, methods of purifying or immobilizing a protein using an affinity tag, and devices for purifying a protein using an affinity tag.

BACKGROUND

The advent of disposable plasmid DNA miniprep kits has revolutionized molecular biology by enabling rapid and inexpensive plasmid purification. While affinity tags for protein purification have been developed, no currently available affinity tag enables rapid, inexpensive protein purification without requiring expensive, specialized reagents (e.g., immobilized binding substrates, immobilized antibodies, nickel nitrilotriacetate resins, etc.).

BRIEF DESCRIPTION OF THE DRAWINGS

Many aspects of the present technology can be better understood with reference to the following drawings. The relative dimensions in the drawings may be to scale with respect to some embodiments. With respect to other embodiments, the drawings may not be to scale. For ease of reference, throughout this disclosure identical reference numbers may be used to identify identical or at least generally similar or analogous components or features.

DETAILED DESCRIPTION

The present technology is generally directed to affinity tags for proteins, proteins comprising an affinity tag, devices configured to purify proteins using affinity tags, and methods of purifying or immobilizing a protein using an affinity tag. In some embodiments, the affinity tag is a silica binding peptide. In some embodiments, the silica binding peptide comprises, consists essentially of, or consists of a peptide of SEQ ID NOs.: 1 to 4. Systems and methods configured in accordance with embodiments of the present technology provide efficient, inexpensive methods of purifying or immobilizing a protein using an affinity tag as disclosed herein.

Selected Embodiments of Affinity Tags and Proteins Comprising Same

The present disclosure provides various affinity tags. Unlike affinity tags known in the art, affinity tags of the present disclosure bind to inexpensive substrates, such as silicon oxide substrates, rather than to antibodies or immobilized metal ions such as nickel nitrilotriacetate. In some embodiments, the silicon oxide substrate comprises, consists essentially of, or consists of silica (e.g., silica gel). In some embodiments, the silicon oxide substrate comprises, consists essentially of, or consists of borosilicate, controlled pore glass, quartz, and/or oxidized silicon.

Figure 1:
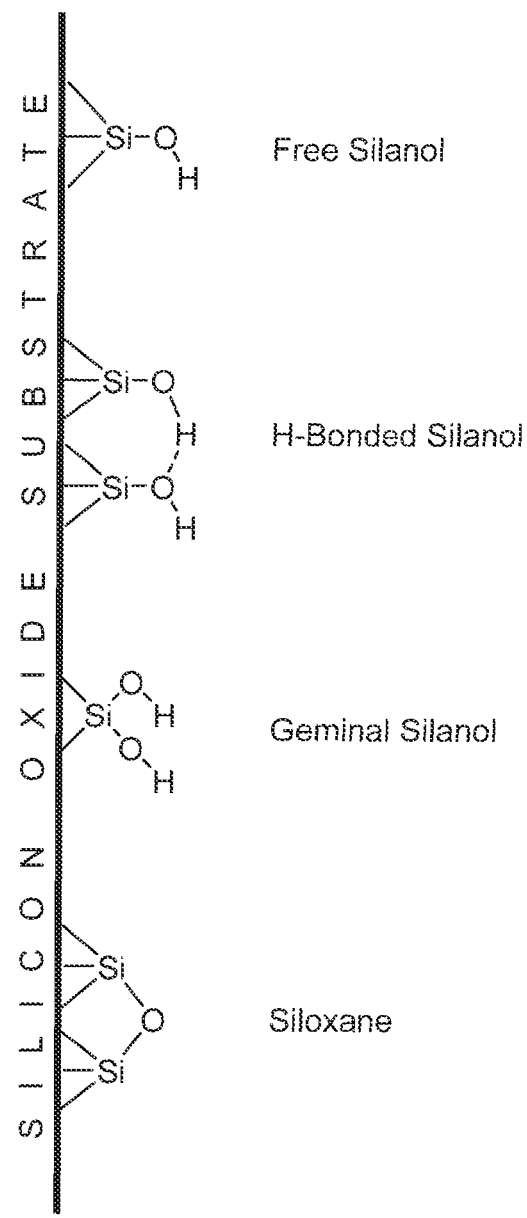
FIG. 1 is a representation of common surface chemistries of silica.

Silicon oxide substrates, as shown representatively in FIG. 1, include several different types of surface silanols and siloxanes. Affinity tags of the present disclosure are configured to releasably bind to the surface of silicon oxide substrates. In some embodiments, the affinity tag has an amino acid sequence of DSARGFKKPGKR (SEQ ID NO.: 1; referred to herein as "Car9"). In other embodiments, the affinity tag has an amino acid sequence of KKRSPILAS-KRR (SEQ ID NO.: 2; referred to herein as "Car8"). In still other embodiments, the affinity tag has an amino acid sequence of RDRGATYPKLGR (SEQ ID NO.: 3; referred to herein as "Car12"). In other embodiments, the affinity tag has an amino acid sequence of RNKRCSSKTRRG (SEQ ID NO.: 4; referred to herein as "Car36"). In other embodiments, the affinity tag has an amino acid sequence of RTYLPLPWMAAL (SEQ ID NO.: 5; referred to herein as "Car15").

In some embodiments, the affinity tag has an amino acid sequence generally homologous to any one of SEQ ID NOs.: 1 to 4, while still exhibiting an affinity for a silicon oxide substrate. In some embodiments, the affinity tag has an amino acid sequence having a homology of at least 70%, at least 80%, at least 90%, or at least 95% with the amino acid sequence of any one of SEQ ID NOs.: 1 to 4.

In one embodiment, the affinity tag has an amino acid sequence having a homology of at least 70% with the amino acid sequence of SEQ ID NO.: 1. In another embodiment, the affinity tag has an amino acid sequence having a homology of at least 80% with the amino acid sequence of SEQ ID NO.: 1; the affinity tag has an amino acid sequence having a homology of at least 90% with the amino acid sequence of SEQ ID NO.: 1. the affinity tag has an amino acid sequence having a homology of at least 95% with the amino acid sequence of SEQ ID NO.: 1. In some embodiments, the affinity tag has an amino acid sequence including a first arginine residue, a hydrophobic residue within two positions of the first arginine residue, two consecutive lysine residues within four positions of the first arginine residue, a third lysine residue within 7 positions of the first arginine residue, and a second arginine residue within 8 positions of the first arginine residue (e.g., XXXRXH$_y$KKXXKR, wherein X is any amino acid residue and H$_y$ is a hydrophobic amino acid residue).

In one embodiment, the affinity tag has an amino acid sequence having a homology of at least 70% with the amino acid sequence of SEQ ID NO.: 2. In another embodiment, the affinity tag has an amino acid sequence having a homology of at least 80% with the amino acid sequence of SEQ ID NO.: 2; the affinity tag has an amino acid sequence having a homology of at least 90% with the amino acid sequence of SEQ ID NO.: 2; the affinity tag has an amino acid sequence having a homology of at least 95% with the amino acid sequence of SEQ ID NO.: 2. In some embodiments, the affinity tag has an amino acid sequence including a first lysine residue, a second lysine residue within 2 positions of the first lysine residue, a first arginine residue within 3 positions of the first lysine residue, at least one hydrophobic residue within 7 positions of the first lysine residue, a third lysine residue within 9 positions of the first lysine residue, a second arginine residue within 10 positions of the first lysine residue, and a third arginine residue within 11 positions of the first lysine residue (e.g., KKRXXH$_y$H$_y$XXKRR, wherein X is any amino acid residue and H$_y$ is a hydrophobic amino acid residue).

In one embodiment, the affinity tag has an amino acid sequence having a homology of at least 70% with the amino acid sequence of SEQ ID NO.: 3. In another embodiment, the affinity tag has an amino acid sequence having a homology of at least 80% with the amino acid sequence of SEQ ID NO.: 3; the affinity tag has an amino acid sequence having a homology of at least 90% with the amino acid sequence of SEQ ID NO.: 3; the affinity tag has an amino acid sequence having a homology of at least 95% with the amino acid sequence of SEQ ID NO.: 3. In some embodiments, the affinity tag has an amino acid sequence including a first arginine residue, a second arginine residue within 3 positions of the first arginine residue, a hydrophobic residue within 6 positions of the first arginine residue, a lysine residue within 8 positions of the first arginine residue, and a third arginine residue within 11 positions of the first arginine residue (e.g., RXRXXXH$_y$XKXXR, wherein X is any amino acid residue and H$_y$ is a hydrophobic amino acid residue).

In one embodiment, the affinity tag has an amino acid sequence having a homology of at least 70% with the amino acid sequence of SEQ ID NO.: 4. In another embodiment, the affinity tag has an amino acid sequence having a homology of at least 80% with the amino acid sequence of SEQ ID NO.: 4; the affinity tag has an amino acid sequence having a homology of at least 90% with the amino acid sequence of SEQ ID NO.: 4; the affinity tag has an amino acid sequence having a homology of at least 95% with the amino acid sequence of SEQ ID NO.: 4. In some embodiments, the affinity tag has an amino acid sequence including a first arginine residue, a first lysine residue within 3 positions of the first arginine residue, a second arginine residue within 4 positions of the first arginine residue, a hydrophobic residue within 5 positions of the first arginine residue, a second lysine residue within 7 positions of the first arginine residue, a third arginine residue within 9 positions of the first arginine residue, and a fourth arginine residue within 10 positions of the first arginine residue (e.g., RXK-RH$_y$XXKXRRX, wherein X is any amino acid residue and H$_y$ is a hydrophobic amino acid residue).

The present disclosure provides proteins comprising an affinity tag as disclosed herein (e.g., any one of SEQ ID NOs.: 1 to 4). In some embodiments, the protein is a fusion protein comprising an affinity tag as disclosed herein and a peptide, such as a therapeutic peptide, a diagnostic peptide, or a peptide of other function. The peptide and the affinity tag may be linked through covalent bonding including, but not limited to, covalent organic bonds (e.g., C—C, C—N, C—O, etc.), disulfide bonding, hydrogen bonding, electrostatic bonding, recombinant fusion, and/or conformational bonding. In some embodiments, the peptide and the affinity tag are linked by one or more linking compounds. In some embodiments, the fusion protein exhibits the same or similar function as the peptide. In some embodiments, the peptide is a polyclonal antibody, a monoclonal antibody, a complement determining region-grafted antibody preparation, a hybrid antibody, an altered antibody, a F(ab)'$_2$ fragment, a Fab molecule, a Fv fragment, a single domain antibody, a chimeric antibody, or a fragment of any of the foregoing. In some embodiments, the peptide is green fluorescent protein ("GFP") or a variant thereof (e.g., GFPmut2). In some embodiments, the peptide is maltose-binding protein ("MBP") or a variant thereof. In some embodiments, the peptide is mCherry fluorescent protein ("mCherry") or a variant thereof.

Proteins of the present disclosure may further comprise a cleavage site, for example a protease cleavage site. In some embodiments, the affinity tag and the peptide of a fusion protein are separated by the cleavage site. In some embodiments, the cleavage site is a portion of the affinity tag. In other embodiments, the cleavage site is a portion of the peptide. In yet other embodiments, the cleavage site comprises, consists essentially of, or consists of an amino acid sequence that is not a portion of the affinity tag or the peptide. In some such embodiments, treatment of the fusion protein with a suitable protease cleaves the affinity tag, or a portion thereof, from the fusion protein to release an amino acid sequence comprising or consisting essentially of the protein. One of skill in the art will recognize that, when a protease is used to cleave the fusion protein, the resulting cleaved peptide will contain at least one terminal amino acid residue in addition to the peptide. For example, a fusion protein of formula $(X)_n$RR-peptide, wherein $(X)_n$RR is the affinity tag having two consecutive arginine residues, and peptide is the peptide, may be cleaved in one embodiment by a protease that targets consecutive basic residues, such as OmpT. In such an embodiment, the fusion protein cleavage products will be $(X)_n$R and R-peptide. In another example, a fusion protein of formula $(X)_n$KK-peptide, wherein $(X)_n$KK is the affinity tag having two consecutive lysine residues, and peptide is the peptide, may be cleaved in one embodiment by a protease that targets consecutive basic residues, such as OmpT. In such an embodiment, the fusion protein cleavage products will be $(X)_n$K and K-peptide.

Proteins of the present disclosure may further comprise a detectable moiety, such as an enzyme, a prosthetic group, a fluorescent material, a luminescent material, a bioluminescent material, a radioactive material, a positron emitting metal, and/or a nonradioactive paramagnetic metal ion. The specific detectable moiety used will depend on the method of detection used; non-limiting examples of detection methods for which a suitable detection moiety may be incorporated into a fusion protein of the present disclosure include: flow cytometric detection, scanning laser cytometric detection, fluorescent immunoassays, enzyme-linked immunosorbent assays (ELISAs), radioimmunoassays (RIAs), bioassays (e.g., neutralization assays), and Western blotting applications. The detection moiety may be linked to the fusion protein through covalent bonding including, but not limited to, covalent organic bonds (e.g., C—C, C—N, C—O, etc.), disulfide bonding, hydrogen bonding, electrostatic bonding, recombinant fusion, and/or conformational bonding. In some embodiments, the detection moiety and the affinity tag are linked by one or more linking compounds.

In some embodiments, a protein of the present disclosure further comprises a marker sequence. The marker sequence, for example, may be linked to the fusion protein through covalent bonding including, but not limited to, covalent organic bonds (e.g., C—C, C—N, C—O, etc.), disulfide bonding, hydrogen bonding, electrostatic bonding, recombinant fusion, and/or conformational bonding. In some embodiments, the marker sequence and the affinity tag are linked by one or more linking compounds. In some embodiments, the marker sequence is selected from: a hexa-histidine tag, a myc tag, and a flag tag.

In some embodiments, a protein of the present disclosure comprises an affinity tag, a peptide, and a cleavage site. The affinity tag and the peptide may be separated by the cleavage site. In some embodiments, the affinity tag has an amino acid sequence at least 70% homologous to or identical to SEQ ID NO.: 1.

In some embodiments, a protein of the present disclosure comprises an affinity tag, a peptide, and a cleavage site. The affinity tag and the peptide may be separated by the cleavage site. In some embodiments, the affinity tag has an amino acid sequence at least 70% homologous to or identical to SEQ ID NO.: 2.

In some embodiments, a protein of the present disclosure comprises an affinity tag, a peptide, and a cleavage site. The affinity tag and the peptide may be separated by the cleavage site. In some embodiments, the affinity tag has an amino acid sequence at least 70% homologous to or identical to SEQ ID NO.: 3.

In some embodiments, a protein of the present disclosure comprises an affinity tag, a peptide, and a cleavage site. The affinity tag and the peptide may be separated by the cleavage site. In some embodiments, the affinity tag has an amino acid sequence at least 70% homologous to or identical to SEQ ID NO.: 4.

Selected Embodiments of Nucleic Acids Encoding Affinity Tags and Proteins Comprising Same The present disclosure provides isolated nucleic acids encoding a protein consistent with the present technology (e.g., a protein comprising an affinity tag, a peptide and a cleavage site). In some embodiments, the isolated nucleic acid comprises RNA or DNA. As used herein, the phrase "isolated nucleic acid" refers to a protein that has been removed from its normal surrounding nucleic acid sequences in the genome or in cDNA sequences, and from which introns (if any) have been removed. Isolated nucleic acids consistent with the present disclosure may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the proteins of the present disclosure.

In some embodiments, the present disclosure provides a recombinant expression vector comprising an isolated nucleic acid disclosed herein operatively linked to a suitable control sequence. As used herein, the phrase "recombinant expression vector" includes vectors that operatively link a nucleic acid coding region or gene to any control sequences capable of effecting expression of the gene product. The term "control sequences" refers to nucleic acid sequences capable of affecting expression of the nucleic acid molecules. As will be recognized by one of skill in the art, a control sequence need not be contiguous with the associated nucleic acid sequence, so long as it functions to direct the expression of the nucleic acid sequence. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art including, but not limited to, plasmid and viral-based expression vectors. The control sequence used to drive expression of the disclosed nucleic acid sequences in a mammalian system may be constitutive (driven by any of a variety of promoters including, but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques, such as those described in Sambrook, Fritsch, and Maniatis, in: *Molecular Cloning, A Laboratory Manual*, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). In general the expression vector must be replicable in a host organism either as an episome or by integration into host chromosomal DNA. In a preferred embodiment, the expression vector comprises a plasmid. However, the scope of the present disclosure includes other expression vectors that serve equivalent functions, such as viral vectors.

In some embodiments, the present disclosure provides a host cell that has been transfected with a recombinant expression vector disclosed herein. The host cells may be prokaryotic (such as bacteria) or eukaryotic. The host cell can be transiently or stably transfected according to any technique known in the art, such as standard bacterial transformations, calcium phosphate co-precipitation, electroporation, or liposome mediated-, DEAE dextran mediated-, polycationic mediated-, or viral-mediated transfection.

The present disclosure provides a method of producing a protein, the method comprising: (a) culturing a host according to this aspect of the invention under conditions conducive to the expression of the protein, and (b) optionally, recovering the expressed protein. The expressed protein can be recovered, for example, by heating host bacterial cells expressing the protein to approximately up to 80° C. Therefore, little to no other physical or chemical step is necessary to release the polypeptides from the cells. Centrifugation eliminates cell debris and aggregates. Purification of the expressed protein from the supernatant may be accomplished by any purification method disclosed herein.

Selected Methods of Purifying Proteins Comprising and Affinity Tag

The present disclosure provides methods for purifying a protein. In some embodiments, the protein is a fusion protein comprising an affinity tag, a peptide, and optionally a cleavage site. Generally, the method of purifying a protein comprises contacting a silicon oxide substrate with a fluid comprising the protein (e.g., fusion protein), contacting the silicon oxide substrate with a washing fluid, and contacting the silicon oxide substrate with a releasing agent to provide the purified fusion protein. The method optionally additionally includes contacting the purified fusion protein with a protease to cleave the affinity tag or a portion thereof from the fusion protein to provide a purified peptide.

The present disclosure also provides methods for purifying a peptide, the method comprising contacting a silicon oxide substrate with a fluid comprising a fusion protein, the fusion protein comprising an affinity tag, a peptide, and optionally a cleavage site; contacting the silicon oxide substrate with a washing fluid; and contacting the silicon oxide substrate with a releasing agent comprising a protease to provide the purified peptide. In some embodiments, the purified peptide additionally includes at least one terminal amino acid residue left over from the cleaved cleavage site and/or from the affinity tag.

The protein to be purified may be any protein that is capable of releasably binding to a silicon oxide substrate as disclosed herein. In some embodiments, the protein is a fusion protein described herein, such as a fusion protein comprising an affinity tag, a peptide, and optionally, a cleavage site.

The step of contacting the silicon oxide substrate may include, for example, contacting a suitable silicon oxide substrate (e.g., silica) with a suspension or solution of a fusion protein including an affinity tag capable of binding to silica. In some embodiments, the silicon oxide substrate (e.g., silica) is housed in a suitable vessel, such as a column, which is formed of a material other than a silicon oxide-based material. In some embodiments, the vessel is a plastic or inert metal vessel.

The step of contacting the silicon oxide substrate with the fluid comprising the protein (e.g., fusion protein) may be performed at a temperature sufficient to enable efficient pouring of the fusion protein suspension or solution while avoiding denaturing of the fusion protein or any portion thereof. Thus, a person of skill in the art will be able to select a suitable temperature based on the peptide(s) of the fusion protein and their sensitivities to elevated temperatures.

The step of contacting the silicon oxide substrate with the fluid comprising the protein (e.g., fusion protein) may be performed for a period of time sufficient to enable complete adsorption of the fusion protein to the silicon oxide substrate. Generally, when the fusion protein includes an affinity tag as disclosed herein, adsorption occurs quickly at room temperature, usually within several minutes. Thus, the step of contacting the silicon oxide may be performed for a period of time of at least about 1 minute, 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 11 minutes, at least about 12 minutes, at least about 13 minutes, at least about 14 minutes, at least about 15 minutes, at least about 16 minutes, at least about 17 minutes, at least about 18 minutes, at least about 19 minutes, at least about 20 minutes, at least about 25 minutes, at least about 30 minutes, at least about 35 minutes, at least about 40 minutes, at least about 45 minutes, at least about 50 minutes, at least about 55 minutes, at least about 60 minutes, or more than 60 minutes.

The step of contacting the silicon oxide substrate with a washing fluid may be performed using any suitable washing fluid capable of flushing any unbound fusion proteins, contaminating proteins, or other undesired components of the fusion protein suspension or solution. When the fusion protein comprises an affinity tag disclosed herein, the washing fluid does not include arginine or lysine, or includes arginine or lysine (individually or combined) at a level below about 0.1M, for example no greater than 0.1M, no greater than about 0.09M, no greater than about 0.08M, no greater than about 0.07M, no greater than about 0.06M, no greater than about 0.05M, no greater than about 0.04M, no greater than about 0.03M, no greater than about 0.02M, no greater than about 0.01M, no greater than about 9 mM, no greater than about 8 mM, no greater than about 7 mM, no greater than about 6 mM, no greater than about 5 mM, no greater than about 4 mM, no greater than about 3 mM, no greater than about 2 mM, or no greater than about 1 mM.

The step of contacting the silicon oxide substrate with a washing fluid may be performed at a temperature sufficient to enable efficient pouring and flow of the washing fluid suspension or solution through the silicon oxide substrate, while avoiding denaturing of the fusion protein or any portion thereof. Thus, a person of skill in the art will be able to select a suitable temperature for the washing step based on the peptide(s) of the fusion protein and their sensitivities to elevated temperatures.

The step of contacting the silicon oxide substrate with a washing fluid may be performed for a period of time sufficient to enable complete flushing of non-adhered contaminants from the silicon oxide substrate. As will be recognized by one of skill in the art, the amount of time required will depend on a number of factors including, for example, the solubility of contaminants in the washing fluid, the viscosity of the washing fluid, the amount of silicon oxide substrate used (e.g., the length of a silica column), the amount of washing fluid to be used, and the pressure applied to the washing fluid (if any) and/or the reduced pressure applied downstream of the silicon oxide substrate (if any). Thus, the step of contacting the silicon oxide with the washing fluid may be performed for a period of time of at least about 1 minute, 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 11 minutes, at least about 12 minutes, at least about 13 minutes, at least about 14 minutes, at least about 15 minutes, at least about 16 minutes, at least about 17 minutes, at least about 18 minutes, at least about 19 minutes, at least about 20 minutes, at least about 25 minutes, at least about 30 minutes, at least about 35 minutes, at least about 40 minutes, at least about 45 minutes, at least about 50 minutes, at least about 55 minutes, at least about 60 minutes, or more than 60 minutes.

The releasing agent used to contact the silicon oxide substrate to release the bound protein (e.g., adhered fusion protein) may comprise a solution or suspension of the releasing agent in a solvent. When the fusion protein includes an affinity tag as disclosed herein, the releasing agent may comprise, consist essentially of, or consist of arginine (e.g., L-arginine) and/or lysine (e.g., L-lysine). The releasing agent may be at any suitable concentration to induce the fusion protein to separate from the silicon oxide substrate. In some embodiments, the releasing agent comprises arginine (e.g., L-arginine) in a concentration of at least about 0.1M, for example at least about 0.1M, at least about 0.2M, at least about 0.3M, at least about 0.4M, at least about 0.5M, at least about 0.6M, at least about 0.7M, at least about 0.8M, at least about 0.9M, at least about 1M, or greater than about 1M. In one embodiment, the releasing agent includes 0.5M arginine (e.g., L-arginine). In another embodiment, the releasing agent includes 1M arginine (e.g., L-arginine).

In some embodiments, the releasing agent comprises lysine (e.g., L-lysine) in a concentration of at least about 0.1M, for example at least about 0.1M, at least about 0.2M, at least about 0.3M, at least about 0.4M, at least about 0.5M, at least about 0.6M, at least about 0.7M, at least about 0.8M, at least about 0.9M, at least about 1M, or greater than about 1M. In a preferred embodiment, the releasing agent includes 0.5M lysine (e.g., L-lysine). In another preferred embodiment, the releasing agent includes 1M lysine (e.g., L-lysine).

Alternatively, the releasing agent may comprise, consist essentially of, or consist of a protease for cleaving the fusion protein, for example at a cleavage site. In some embodiments, the protease is selected to cleave the fusion protein at a cleavage site between the affinity tag and the peptide. In other embodiments, the protease is selected to cleave the fusion protein at a cleavage site within the affinity tag. In still other embodiments, the protease is selected to cleave the fusion protein at a cleavage site within the peptide. In some embodiments, the releasing agent comprises, consists essentially of, or consists of a protease selective for a cleavage site at or near the C-terminal or N-terminal of the affinity tag (e.g., whichever terminus is covalently bound to the peptide of a fusion protein). In some embodiments, the releasing agent comprises, consists essentially of, or consists of a protease selected from the group consisting of: OmpT, TEV protease, Thrombin, Factor Xa and Enterokinase.

The step of contacting the silicon oxide substrate with a releasing agent to release the bound protein (e.g., adhered fusion protein) or to cleave the peptide from the fusion protein (e.g, on-gel cleavage) may be performed at a temperature sufficient to enable efficient pouring of the releasing agent suspension or solution while avoiding denaturing of the fusion protein or any portion thereof. Thus, a person of skill in the art will be able to select a suitable temperature based on the peptide(s) of the fusion protein and their sensitivities to elevated temperatures.

The step of contacting the silicon oxide substrate with the releasing agent may be performed for a period of time sufficient to enable complete desorption of the fusion protein from the silicon oxide substrate or cleavage of the peptide from the fusion protein. Generally, when the fusion protein includes an affinity tag as disclosed herein, desorption occurs quickly at room temperature, usually within several minutes, depending on the concentration and flow rate of the releasing agent. Thus, the step of contacting the silicon oxide may be performed for a period of time of at least about 1 minute, 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 11 minutes, at least about 12 minutes, at least about 13 minutes, at least about 14 minutes, at least about 15 minutes, at least about 16 minutes, at least about 17 minutes, at least about 18 minutes, at least about 19 minutes, at least about 20 minutes, at least about 25 minutes, at least about 30 minutes, at least about 35 minutes, at least about 40 minutes, at least about 45 minutes, at least about 50 minutes, at least about 55 minutes, at least about 60 minutes, or more than 60 minutes.

EXAMPLES

Example 1

Assay for Determining Binding Affinity to Silica

A surface plasmon resonance ("SPR") experiment was conducted using TrxA::Car9 (SEQ ID NO.: 6), a derivative of *E. coli* thioredoxin (TrxA) including a disulfide-constrained Car9 sequence flanked by Cys-Gly-Pro and Gly-Cys-Pro tripeptides in place of thioredoxin's native Cys-Gly-Pro-Cys active site. This fusion protein was expressed along with wild type TrxA (SEQ ID NO.: 7).

Silica-coated SPR chips were prepared by chemical vapor deposition (CVD) to deposit a thin (~3 nm) silica film onto gold-coated SPR chips. The silica-coated SPR chips were washed with ethanol and adsorbed organic matter was removed by exposure to UV-ozone for 20 minutes. Solutions of TrxA and TrxA::Car9 (1 µM each) were simultaneously flowed over the chip using a multichannel apparatus. The SPR chips were washed with buffer for 10 minutes to remove loosely bound protein.

Figure 2:
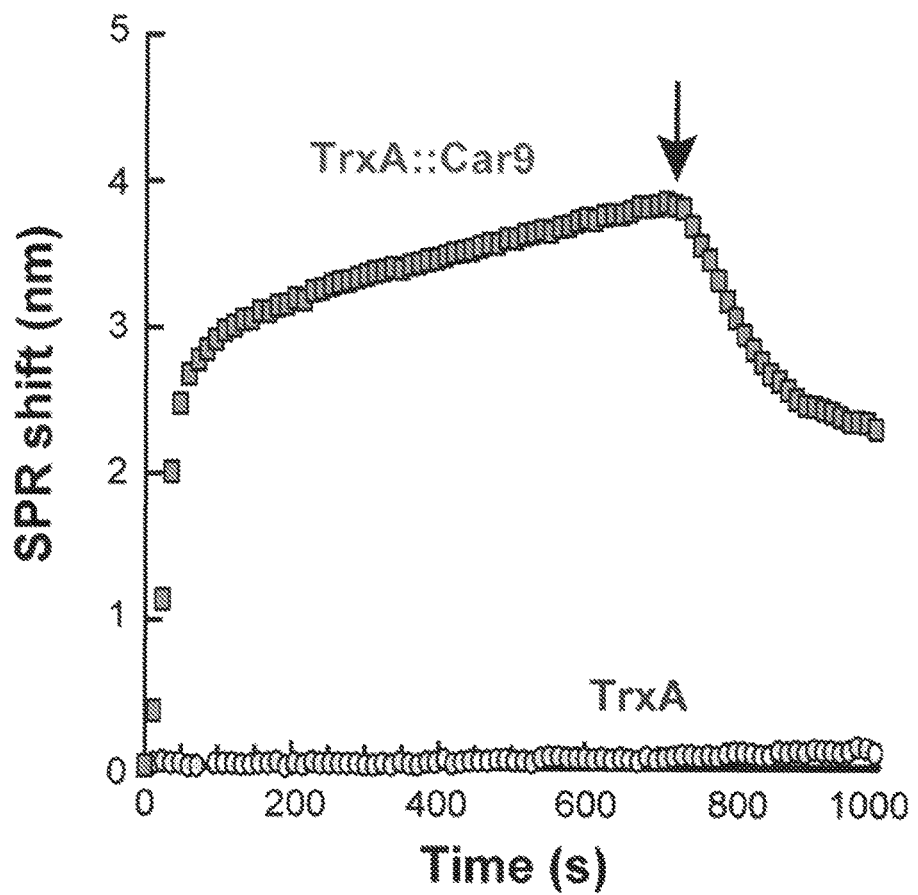
FIG. 2 is a plot showing a surface plasmon resonance ("SPR") analysis of adsorption of TrxA::Car9 onto a silica-coated SPR chip compared to TrxA over a 12-minute adsorption phase (1 μM reagent concentration at 50 μL/min flow rate), followed by a 10-minute buffer-only wash cycle (arrow).

As shown in FIG. 2, TrxA::Car9 rapidly adsorbed to the silica-coated SPR chips; more than 50% of the bound protein remained on the silica surface after washing. In contrast, TrxA did not bind. These data indicate that disulfide-constrained Car9 confers silica binding affinity to TrxA protein.

Example 2

Affinity of Car9 for Silica

To determine if presentation in a disulfide-bonded loop is required for Car9 to bind silica and to facilitate the construction of fusion proteins containing a C-terminal Car9 extension, a cassette specifying a HindIII restriction site, a Gly-Gly-Gly-Ser linker and the Car9 dodecamer was inserted into plasmid pBLN200, a pET-24a(+) (Novagen) derivative in which the T7 promoter was replaced by a DNA segment encoding the araC gene and the arabinose-inducible $P_{BAD}$ promoter. The resulting plasmid was named pBLN200-Car9 (SEQ ID NO.: 8).

A NdeI-HindIII cassette encoding the green fluorescent protein (GFP) variant GFPmut2 was next cloned into the same sites of pBLN200-Car9. Both authentic GFPmut2 (SEQ ID NO.: 9) and the derivative containing the Car9 extension at its C-terminus (SEQ ID NO.: 10 hereinafter referred to as GFPmut2-Car9) were expressed at high level and in a soluble form in *E. coli* BL21(DE3), purified by anion exchange chromatography, and dialyzed against 20 mM Tris-HCl pH 7.5.

Figure 3A:
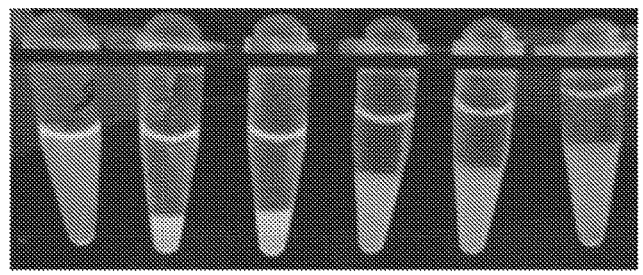
FIGS. 3A and 3B show centrifuge tubes containing hydrated silica gel (60-220 μm) after one hour of incubation at room temperature with 150 μL (2.2 μM) of GFPmut2 (FIG. 3A) or GFPmut2-Car9 (FIG. 3B).
Figure 3B:
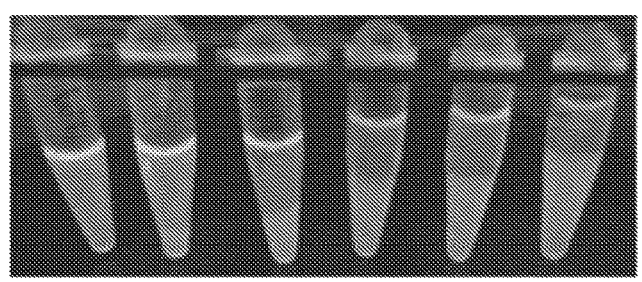
Figure 3C:
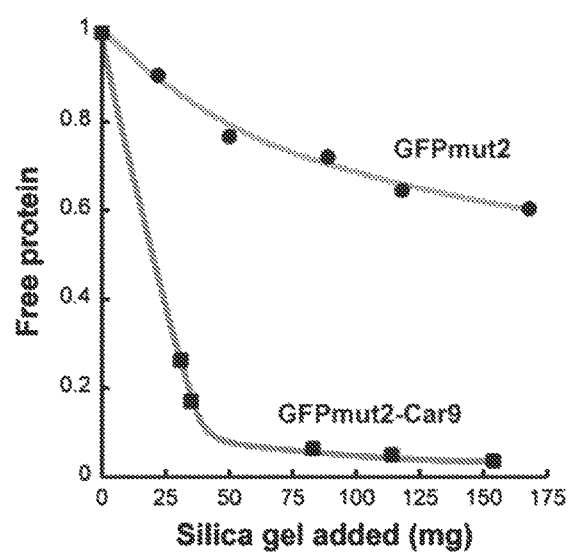
FIG. 3C is a plot of free GFP protein in the supernatant fluids of FIGS. 3A-3B as a function of the amount of silica gel added.

GFPmut2-Car9 and GFPmut2 (as a control) were incubated separately with increasing amounts of silica gel for 1 hour, and the amount of unbound protein was quantified by assaying the supernatant by fluorescence spectroscopy. FIG. 3A shows that while GFPmut2 exhibited the characteristic behavior of a protein that adsorbs non-specifically to a solid, FIG. 3B demonstrates that GFPmut2-Car9 could be depleted from solution upon addition of small amounts of silica. In fact, while about 35 mg of silica gel was sufficient to capture all soluble GFPmut2-Car9 under these experimental conditions, data extrapolation indicates that more than 10 times that amount would be needed to quantitatively adsorb all GFPmut2 (FIG. 3C).

Figure 4:
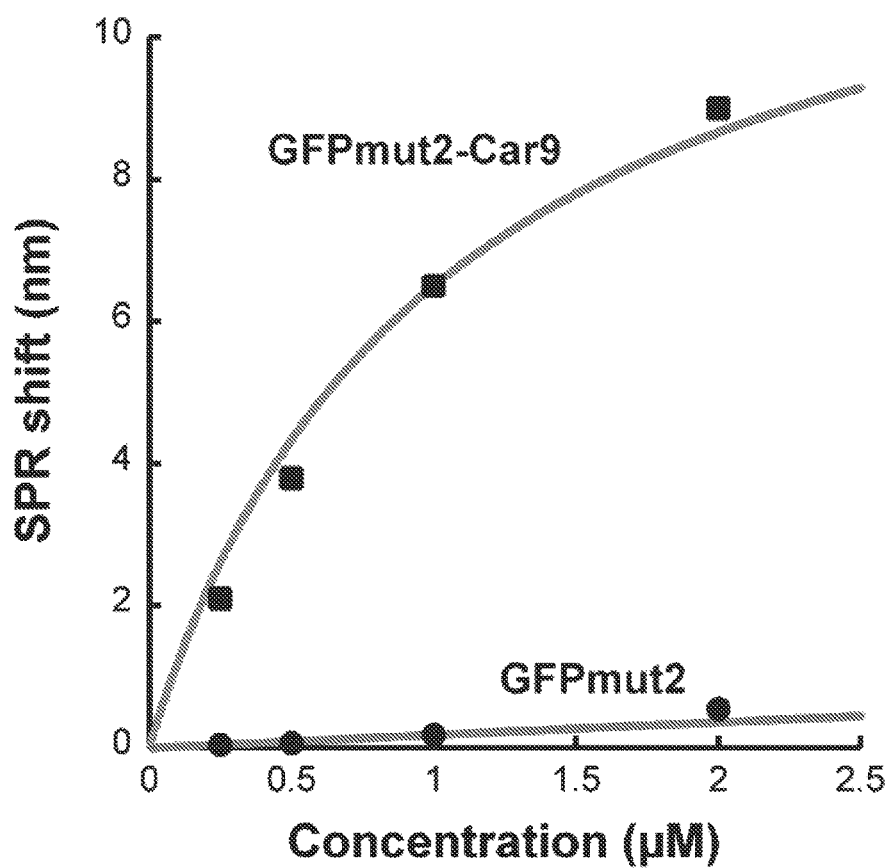
FIG. 4 is a plot of Langmuir absorption isotherm constructed by plotting the SPR shift in nanometers induced by the binding of GFPmut2-Car9 (■) and GFPmut2 (■) on silica as a function of the protein concentration. Solid lines indicate theoretical fits using Langmuir adsorption kinetics.

To more accurately quantify the affinity of the Car9 tag for silica, a series of SPR experiments were conducted on silica-coated chips prepared according to Example 1 at increasing protein concentrations. Consistent with the results discussed above, GFPmut2 had little affinity for the silica-coated SPR chip surface (FIG. 4, -●-) By contrast, GFPmut2-Car9 adhered to the silica film in a concentration-dependent manner (FIG. 4, -■-) and with a $K_d$ of 1 µM. This equilibrium dissociation constant is identical to that exhibited by hexahistidine-tagged proteins for Ni-NTA. These data demonstrate that Car9 retains its ability to bind silica when in a linear conformation and that it does not induce GFP misfolding, as was expected from its hydrophilic and basic nature.

Example 3

Purification of Proteins Using Affinity Tags

*E. coli* SF100 cells, which are deficient in the outer membrane associated protease OmpT, harboring plasmid pGFPmut2-Car9 were grown overnight at 37° C. in 25 mL Luria Broth (LB) supplemented with 50 µg/mL kanamycin. Seed cultures were used to inoculate 500 mL of LB medium, and cells were grown to $A_{600} \approx 0.5$ at 37° C. Cultures were transferred to a 25° C. water bath for 10 minutes and protein synthesis was induced by supplementing the medium with 2% L-Arabinose. After 6 hours of cultivation at the same temperature, cells were harvested by centrifugation at 7,000 g for 5 minutes, resuspended in 35 mL of 20 mM Tris-HCl pH 7.5 supplemented with 2 mM EDTA, and disrupted by 6 rounds of sonication for 3 minutes each at 30% duty cycle using a Branson sonifier. Lysates were clarified by centrifugation at 10,000 g for 15 minutes.

Figures 5A, 5B:
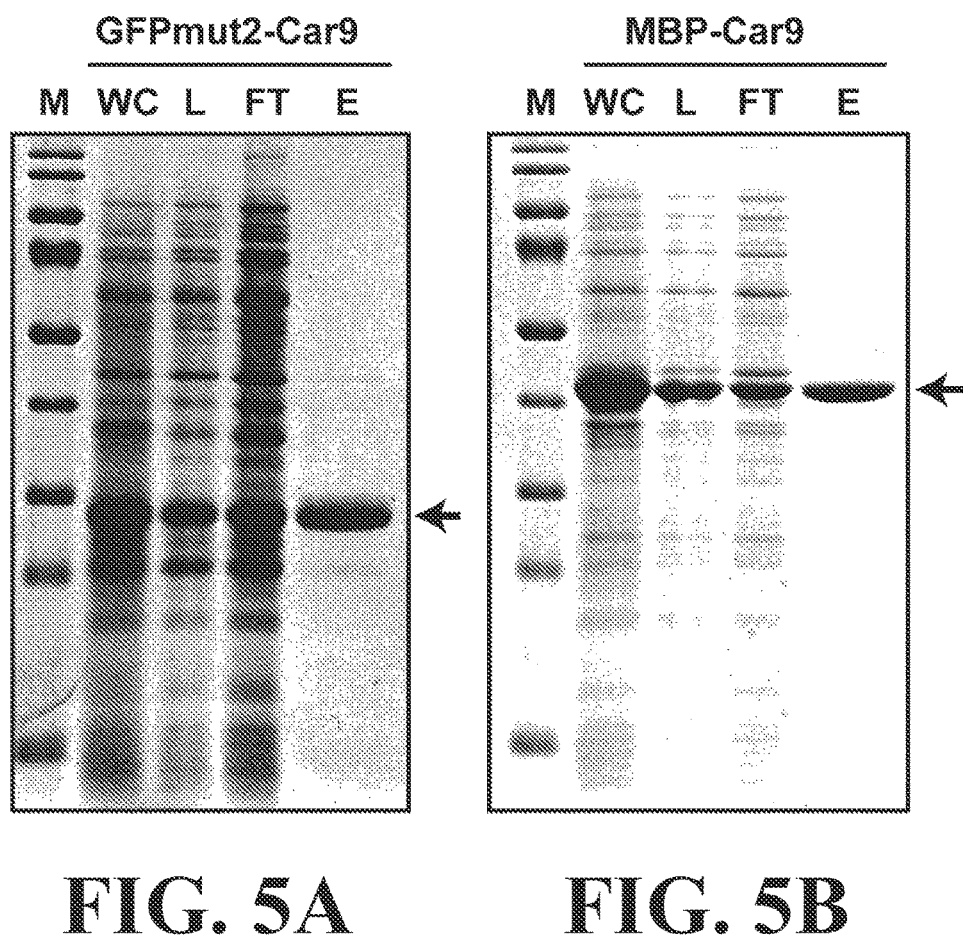
FIGS. 5A and 5B show results of purification of GFPmut2-Car9 (FIG. 5A) and MBP-Car9 (FIG. 5B) by silica gel chromatography and 0.5M arginine elution. Lanes show whole cell lysates (WC), clarified lysates (L) flow through (FT) and eluted fractions (E). Arrows indicate purified protein.
Figure 6:
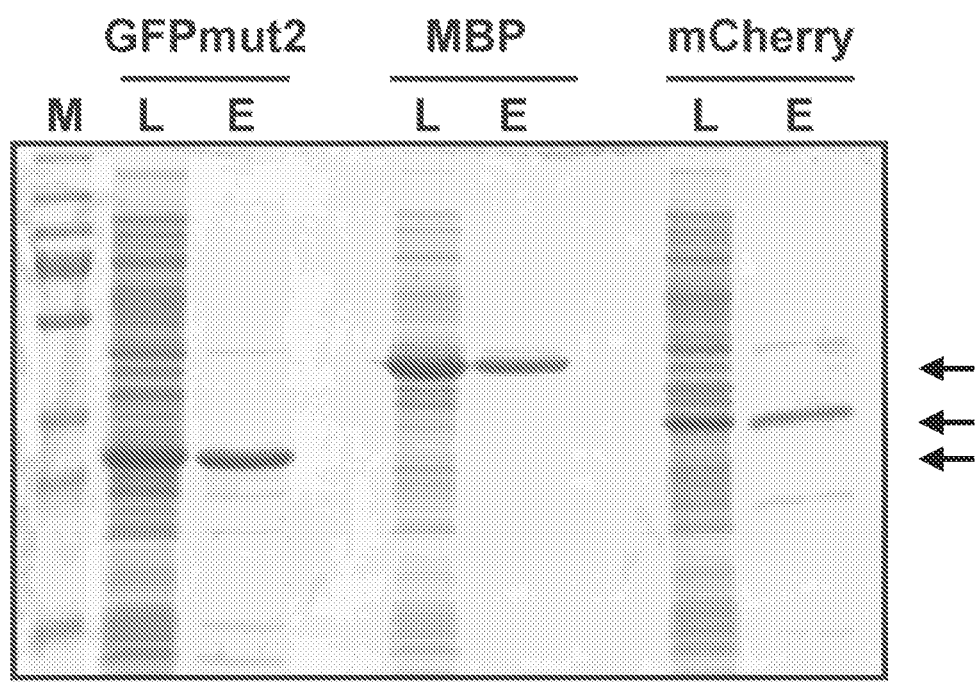
FIG. 6 shows results of purification of GFPmut2-Car9, MBP-Car9 (labelled "MBP" in FIG. 6) and mCherry-Car9 (labelled "mCherry" in FIG. 6) by silica gel chromatography and 1M lysine elution. Lanes show clarified lysate (L) and eluted fractions (E). Arrows indicate the position of purified protein.

For initial experiments, an aliquot (5 mL) of clarified lysate was mixed overnight at 8° C. and with gentle agitation with 3 g of silica gel (63-200 µm spherical particles with 6 nm pore size; cat. no. 391484, Sigma-Aldrich, St. Louis, Mo.). The protein-loaded resin was loaded onto a 1 cm inner diameter chromatography column (Pharmacia) and washed at 1 mL/min with 20 mM Tris-HCl pH 7.5 until no protein was detected in the effluent. Addition of up to 5M NaCl or $MgCl_2$ proved ineffective at releasing the bound protein. However, supplementing the buffer with 0.5M arginine resulted in quantitative elution of highly pure GFPmut2-Car9 (FIG. 5A). A repeat of the experiment is shown in FIG. 6 (middle two lanes labelled "MBP"). These data seem to suggest that the guanidium group of arginine is an effective competitor of the electrostatic and H-bonding interactions that stabilize Car9-silica interactions.

A NdeI-HindIII cassette encoding maltose binding protein (MBP) was cloned into pBLN200-Car9. The resulting protein, MBP-Car9 (SEQ ID NO.: 11), was expressed at high level and in a partially soluble form in *E. coli* SF100 as described in section. An aliquot (5 mL) of clarified lysate was mixed overnight at 8° C. and with gentle agitation with 3 g of silica gel (63-200 µm spherical particles with 6 nm pore size; cat. no. 391484, Sigma-Aldrich, St. Louis, Mo.). The protein-loaded resin was loaded onto a 1 cm inner diameter chromatography column (Pharmacia) and washed at 1 mL/min with 20 mM Tris-HCl pH 7.5 until no protein was detected in the effluent. Supplementing the buffer with 0.5M arginine resulted in quantitative elution of highly pure MBP-Car9 (FIG. 5B).

A NdeI-HindIII cassette encoding the fluorescent protein mCherry with a N-terminal hexa-histidine tag was cloned into pBLN200-Car9. The resulting protein, mCherry-Car9 (SEQ ID NO.: 12), was expressed at high level and in a partially soluble form in *E. coli* SF100 as described above. An aliquot (5 mL) of clarified lysate was mixed overnight at 8° C. and with gentle agitation with 3 g of silica gel (63-200 µm spherical particles with 6 nm pore size; cat. no. 391484, Sigma-Aldrich, St. Louis, Mo.). The protein-loaded resin was loaded onto a 1 cm inner diameter chromatography column (Pharmacia) and washed at 1 mL/min with 20 mM Tris-HCl pH 7.5 until no protein was detected in the effluent. Supplementing the buffer with 0.5M arginine resulted in quantitative elution of highly pure mCherry-Car9 (FIG. 6, right two lanes labelled "mCherry").

Clarified extracts from SF100 cells expressing GFPmut2-Car9 ("GFPmut2" in FIG. 6), MBP-Car9 ("MBP" in FIG. 6) or mCherry-Car9 ("mCherry" in FIG. 6) were prepared as described above. Aliquots (5 mL) of clarified lysates were mixed overnight at 8° C. and with gentle agitation with 3 g of silica gel (63-200 µm spherical particles with 6 nm pore size; Sigma). Each preparation of protein-loaded resin was loaded onto a 1 cm inner diameter chromatography column (Pharmacia) and washed at 1 mL/min with 20 mM Tris-HCl pH 7.5 until no protein was detected in the effluent. Supplementing the buffer with 1.0M L-lysine resulted in quantitative elution of highly pure GFP-mut2, MBP-Car9 and mCherry-Car9 (FIG. 6).

Example 4

Rapid Purification from Crude Cellular Extracts Using Affinity Tags

Figure 7A:
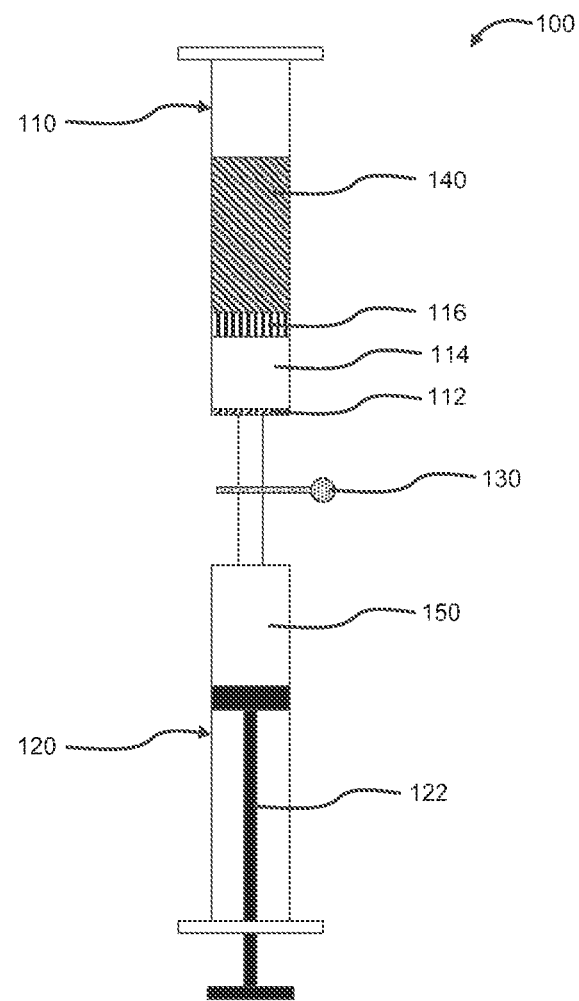
FIG. 7A illustrates a partially schematic view of a device for purifying a protein configured according to one embodiment of the present technology.

A device 100 consistent with that shown in FIG. 7A was constructed using two 30-mL syringes 110, 120 tethered to each other by a valve 130. The valve 130 was closed and a glass wool plug 112 was inserted into the first syringe 110. About 3 g of silica gel was loaded into the first syringe 110, on top of which a perforated plastic screen 116 was placed.

90 mL of 20 mM Tris-HCl at pH 7.5 was loaded into the first syringe 110 to wash the matrix 112-116. The buffer was removed by pulling on the plunger 122 of the second syringe 120. 0.5 mL of clarified extract 140 from induced SF100 (pGFPmut2-Car9) cultures was loaded into the first syringe 110 and flowed through the matrix 112-116 by pulling the plunger 122. 90 mL of buffer supplemented with 1M L-lysine was then added to the first syringe 110 and drawn through the matrix 112-116 by pulling on the plunger 122 to yield purified protein 150.

Figure 7B:
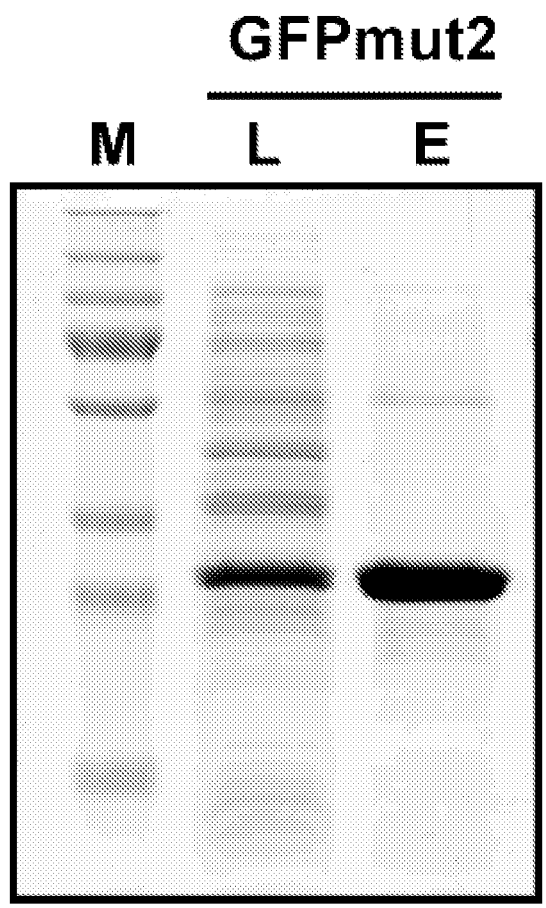
FIG. 7B shows results of purification of GFPmut2-Car9 with 1M L-lysine eluent using a device configured according to one embodiment of the present technology. Lanes indicate clarified lysate (L) and eluted fractions (E) after 50-fold concentration.

As shown in FIG. 7B, the purified protein 150 (lane "E") essentially included only the GFPmut2-Car9 fusion protein. The lysate (lane "L") included a small amount of the GFPmut2-Car9 fusion protein along with other impurities. The entire process of purifying the lysate was accomplished in less than 15 minutes.

Example 5

Cleavage of Affinity Tags in Cell Lysates

OmpT is an aspartate protease that exhibits narrow specificity for paired basic residues. It is located in the outer membrane of *E. coli* K12 strains but absent in *E. coli* B strains (e.g., BLD1); cell integrity must be disrupted in order for OmpT to have access to intracellular substrates. The Car9 sequence contains two sets of paired basic residues: an internal Lys-Lys and a C-terminal Lys-Arg sequence. In addition, fusion of the Car9 to the C-terminus of GFPmut2 via a Gly-Gly-Gly-Ser linker introduces a Lys-Lys dipeptide at the fusion joint. To determine if these sites would be accessible to OmpT, GFPmut2-Car9 and MBP-Car9 were expressed as described above, except that the ompT$^+$ strains KS272 (F' ΔlacX74 galE galK thi rpsL(strA) ΔphoA) and Top10 (F$^-$ endA1 recA1 hsdR17 ($r^-_k, m^+_k$) λ$^-$supE44 thi1 gyrA96 relA1 φ80ΔlacΔM15Δ(lacZYA-argF)U169 deoR) were used. Expressed fusion protein was assayed according to the protocol of Example 3, except that the lysates were held for 30 minutes on ice to allow membrane-associated OmpT to access its potential substrates.

Figure 8A:
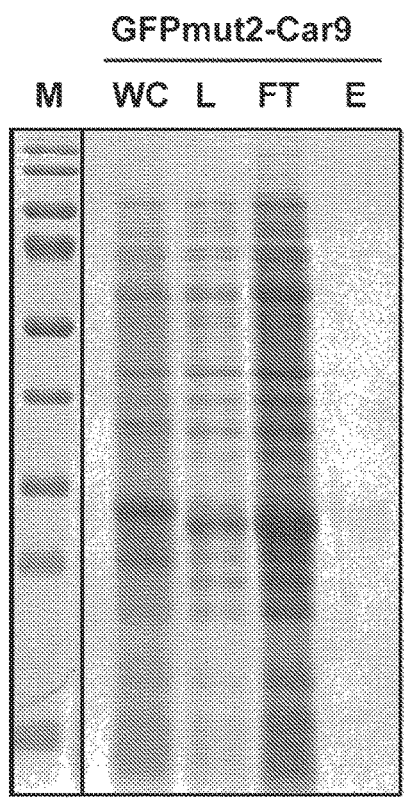
FIGS. 8A and 8B show results of purification of GFPmut2-Car9 from KS272 cells and MBP-Car9 from Top10 cells, respectively, using 3 g of silica gel and 0.5M arginine eluent after sonication and incubation of the lysates on ice for 30 minutes in the presence of OmpT. Lanes show whole cell (WC), clarified lysates after 30 minutes of incubation (L), flow through (FT), and eluted fractions (E). In each of FIGS. 8A and 8B, the top arrow indicates the migration position of intact GFPmut2-Car9 and MBP-Car9, respectively, while the bottom arrows indicate the migration position of the degradation products.
Figure 8B:
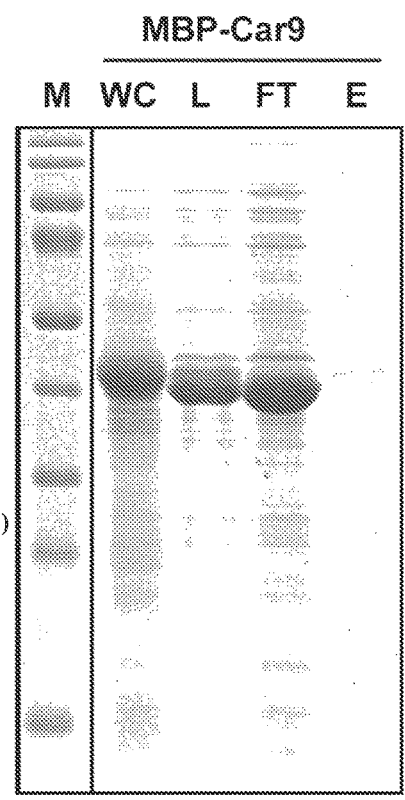

As shown in FIGS. 8A and 8B, whole cell lysates (lanes "WC") indicated the presence of intact GFPmut2-Car9 and MPR-Car9, indicated by the asterisked arrows, ←*. A lower molecular weight product, indicated by the daggered arrows, ←(†), accumulated in lysed fractions (lanes "L") did not show affinity for silica; these products flowed through the silica gel (lanes "FT") and were not released from silica by the 1M lysine eluent (lanes "E").

These data indicate that the Car9 affinity tag is solvent/protease accessible, and that the terminal Lys-Pro-Gly-Lys-Arg sequence contributes to silica adhesion. In addition, these data suggest that OmpT could be used to remove almost half of a C-terminal Car9 affinity tag from a fusion protein such as MBP-Car9 or all of the affinity tag from a fusion protein such as GFPmut2-Car9 instead of more expensive site-specific proteases (e.g., thrombin, factor Xa, TEV protease, etc.). Similarly, OmpT digestion may be used to remove nearly all of an N-terminal Car9 affinity tag (i.e., only the terminal arginine residue would remain). Thus, purification of a fusion protein comprising a Car9 affinity tag by silica gel chromatography, followed by OmpT digestion, can rapidly and inexpensively provide purified proteins.

Example 6

Cleavage of Affinity Tags Within Intact Cells

To determine if the OmpT protease would be useful within the context of intact cells to inexpensively remove the Car9 affinity tag, SF100 cells transformed or not with pML19 (SEQ ID NO.: 13), a multicopy plasmid encoding OmpT, were grown at 37° C. in 25 mL of LB medium supplemented with 100 μg/mL carbenicillin. After 5 h of growth at 37° C., cells were harvested from culture volumes corresponding to 3 absorbance units at 600 nm ($A_{600}$) and washed 3 times with 2 mL of 50 mM sodium phosphate pH 7.5 with intervening 5000 g centrifugation steps. After the final wash, cells were resuspended in 100 μL of 50 mM phosphate buffer pH 7.5 containing purified GFPmut2-Car9 at 10 μM final concentration. After 30 or 45 min incubation at room temperature, cells were sedimented at 5000 g, and aliquots of the supernatants were fractionated by SDS-PAGE.

Figures 9A, 9B:
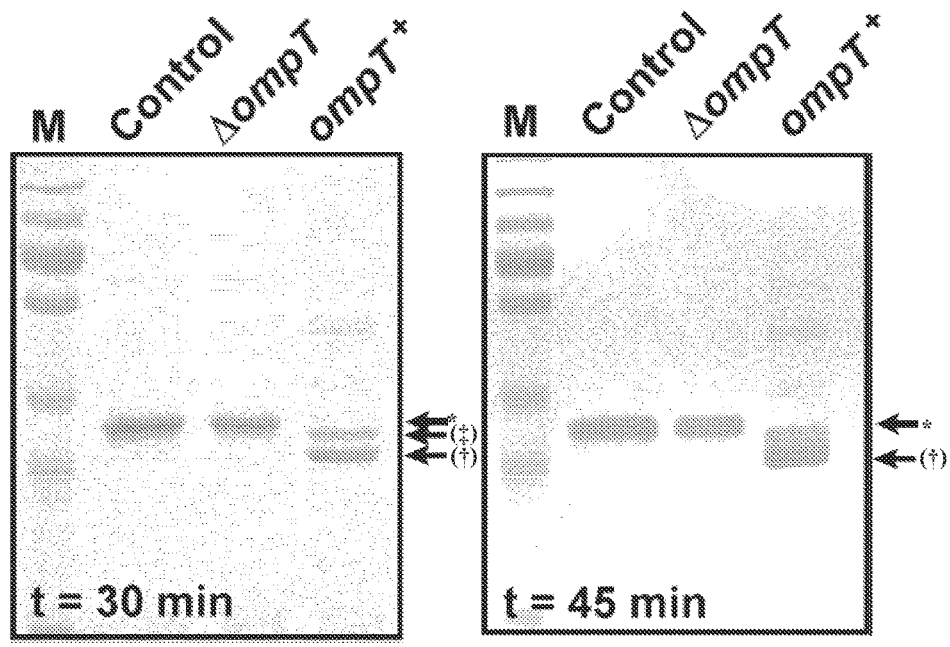
FIGS. 9A and 9B show the results of incubating purified GFPmut2-Car9 (Control) with whole cells lacking (ΔompT) or overproducing (ompT$^+$) the outer membrane protease OmpT. Soluble proteins were subjected to SDS-PAGE analysis after 30 minutes (FIG. 9A) or 45 minutes (FIG. 9B) of incubation at room temperature and removal of the cells.

FIG. 9A shows that, while the fusion protein remained intact when placed in contact with ΔompT cells (gray, asterisked arrow), it was converted into its expected degradation products (black, daggered arrows) after 30 min of incubation with OmpT-overproducing cells. In addition, tag-free GFPmut2 was the dominant product after 15 additional minutes of incubation (FIG. 9B, daggered arrow).

Example 7

Cost of Use

Because the present technology utilizes inexpensive, unmodified silica gel instead of a specialty solid phase, the cost to purify a protein is significantly lower than presently available alternatives. Purification of about 15 mg of purified protein using methods disclosed herein may require about 3 g of silica. Thus, purification reagent costs are estimated to be on the order of US$1.50 per 10 mg of purified protein. In contrast, purifying the same amount of His-tagged protein using Ni-NTA technology, the least expensive alternative widely available at this time, would cost more than 10 times that amount.

Example 8

Functionalization of Glass Surfaces Using Fusion Proteins

Decorating glass, borosilicate and silicon with proteins is important in sensor and microarray development, as well as for electronic, bioimaging and medical applications. Typically, silane coupling agents terminated with an amino (e.g., aminopropylsilane) or a thiol (e.g., mercaptopropylsilane) group that is suitable for subsequent protein conjugation. The affinity tags disclosed herein (e.g., Car9) may be used instead to functionalize silica surfaces by simply contacting the silica surface with a solution of a fusion proteins as disclosed herein. Unlike functionalization using a traditional silane coupling agent, the use of a fusion protein additionally enables oriented immobilization (through the tagged end of the fusion protein) and selective release (by addition of arginine or lysine).

Figure 10A:
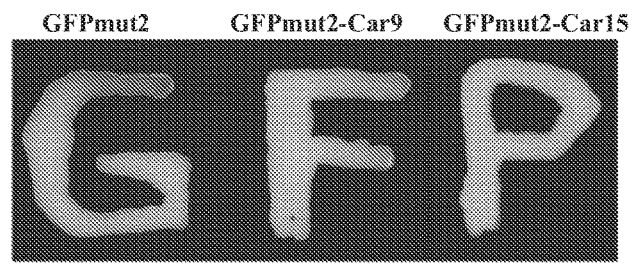
FIG. 10A shows a silica slide after incubation for one minute with 15 μL of a 10 μM solution of GFPmut2 (left region), GFPmut2-Car9 (middle region) and GFPmut2-Car15 (right region).
Figure 10B:
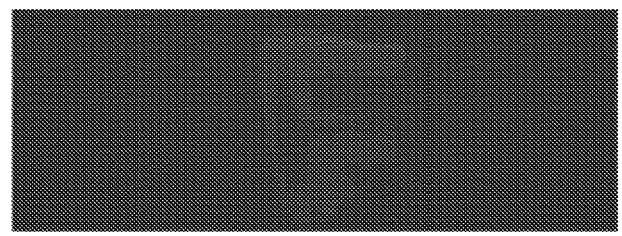
FIG. 10B shows the slide of FIG. 10A after washing for 5 minutes with ddH$_2$O.
Figure 10C:
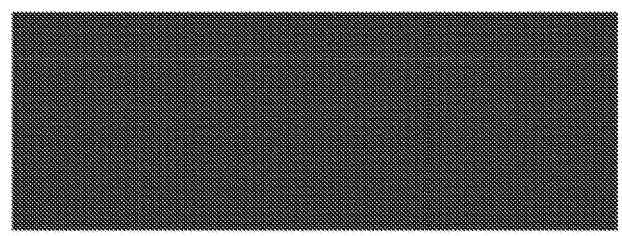
FIG. 10C shows the slide of FIG. 10B after washing for 5 minutes with 0.5M arginine in buffer. In each of FIGS. 10A-10C, the slide was imaged under wet conditions using a Typhoon 9000 gel imaging scanner with excitation at 488 nm.

In one exemplary illustration of the above, aliquots of 10 µM solutions of GFPmut2, GFPmut2-Car9 and GFPmut2-Car15 (a derivative a GFPmut2 fitted with the Arg-Thr-Tyr-Leu-Pro-Leu-Pro-Trp-Met-Ala-Ala-Leu carbon binding sequence Car15 (SEQ ID NO.: 5) in place of Car9; SEQ ID NO.: 14) were deposited using a toothpick onto a glass microscope slide that had been cleaned with ddH$_2$O and dried. Imaging with a GE Typhoon FLA 9000 scanner revealed that equivalent amount of fluorescent material had been deposited onto the surface (FIG. 10A). After a 5 minute wash in ddH$_2$O with gentle shaking, all GFPmut2 and most of GFPmut2-Car15 had been removed, while a monolayer of GFPmut2-Car9 remained adhered to the glass slide (FIG. 10B). Immersion of the slide in 20 mM Tris-HCl at pH 7.5 supplemented with 0.5M L-arginine led to almost complete release of the adsorbed protein (FIG. 10C), confirming glass adhesion of the fusion protein through the Car9 affinity tag. These data indicate that the Car9 affinity tag represents a straightforward one-step alternative to silane chemistry for functionalizing silica surfaces. In addition, and unlike silane chemical techniques, functionalization of glass surfaces with a fusion protein as disclosed herein is chemically reversible.

Example 9

Identification of Additional Releasable Affinity Tags

*E. coli* GI826 cells (F$^-$ lacI$^q$ ampC::P$_{trp}$cI ΔfliC ΔmotB eda::Tn10) lacking a plasmid or transformed with derivatives of plasmid pFliTrx (Invitrogen) specifying Car8, Car9, Car12 or Car36 flanked by a N-terminal Cys-Gly-Pro tripeptide and a C-terminal Gly-Pro-Cys tripeptide, and inserted within the FliTrx protein (SEQ ID NO.: 15; a synthetic, cell surface exposed fusion protein; Invitrogen) were grown in 5 mL of IMC medium (6 g of Na$_2$HPO$_4$, 3 g of KH$_2$PO$_4$, 0.5 g of NaCl, and 1 g of NH$_4$Cl in 1 L of deionized water with 0.2% casamino acids, 0.5% glucose and 1 mM MgCl$_2$) supplemented with 100 µg/mL carbenicillin for 24 h at 25° C. Culture aliquots (1 mL) were used to inoculate 125 mL shake flasks containing 25 mL of IMC medium supplemented with 100 µg/mL carbenicillin. Cells were grown at 25° C. to A$_{600}$≈0.5 and the synthesis of FliTrx::Car8 (SEQ ID NO.: 16), FliTrx::Car9 (SEQ ID NO.: 17), FliTrx::Car12 (SEQ ID NO.: 18) and FliTrx::Car36 (SEQ ID NO.: 19) was induced by addition of 0.1 mg/mL L-tryptophan. Cultivation was continued for 5 hours or more and until A$_{600}$ exceeded 1. The turbidity of all cultures was then adjusted to 1.0 using IMC medium.

Aliquots of these solutions (2 mL) were transferred in duplicate to the wells of 24-wells cell culture plates containing a ~1×1 cm piece of glass microscope slide (VWR). After 15 minutes of incubation at room temperature with gentle agitation, the liquid was aspired and 2 mL of Buffer A (20 mM Tris-HCl, pH 7.5) was added as wash. After 1 minute, the liquid was aspired. This wash cycle was repeated 2 additional times.

Duplicate samples were then treated with either 2 mL of Buffer A or 2 mL of Buffer A supplemented with 1M L-lysine. After 10 minutes incubation at room temperature with gentle agitation, the glass slides were removed, transferred to the stage of an optical microscope, and cells present in 3 different fields were counted at 90× magnification. This number was averaged to represent one measurement. The experiment was replicated three times in its entirety.

Figure 11:
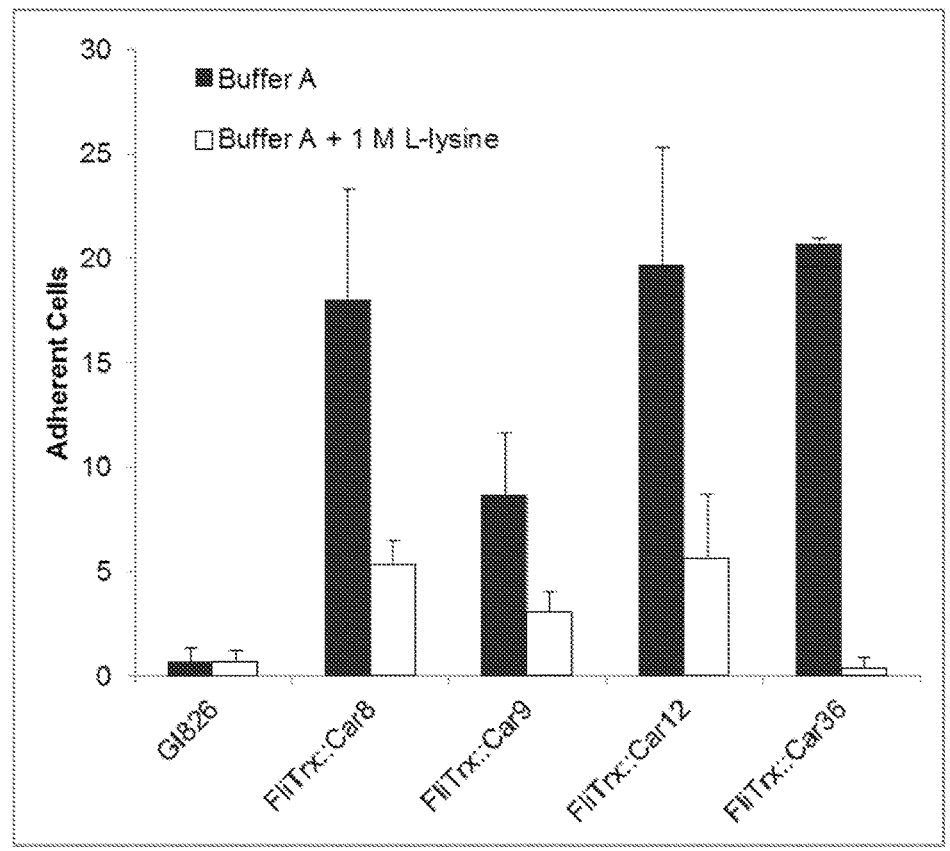
FIG. 11 shows results of a cellular adherence experiment indicating that Car8, Car9, Car12 and Car 36 all bind to silica and can be removed upon treatment with 1M L-lysine solution in 20 mM Tris buffer at pH 7.5.

FIG. 11 shows that, in addition to the FliTrx::Car9 positive control, the FliTrx::Car8, FliTrx::Car12 and FliTrx::Car36 fusion proteins enable efficient cell attachment to microscope glass slides. By contrast, plasmid-free cells that do not express any FliTrx fusion protein on their surface ("GI826" in FIG. 11) do not appreciably adhere to the glass. FIG. 11 also shows that incubation with 1M L-lysine partially (FliTrx::Car8; FliTrx::Car9; FliTrx::Car12) or efficiently (FliTrx::Car36) precludes cell attachment to glass, demonstrating that L-lysine and/or arginine triggers release of the Car8, Car12 and Car36 affinity tags from silica-containing surfaces.

Example 10

Immobilization and Controlled Release of Proteins from Silica Sol-Gels

Sols are dispersions of colloidal particles in a liquid phase that can be polymerized into a rigid mass known as a gel through a variety of chemistries. The resulting porous networks can be used as matrices to entrap enzymes, proteins or other payloads for applications ranging from biosensing to controlled drug delivery. Some of the problems of these technologies include loss of bioactivity over time and uncontrolled leaking of adsorbed proteins into the surrounding medium.

A silica sol-gel was prepared according to standard methods. Briefly, 5.4 mL of concentrated NH$_4$OH was added to 1 L of water, and 5 mL of the solution was mixed with 10 mL of methanol in a beaker to produce a catalyst solution. Separately, 10 mL of tetramethoxysilane (TMOS) was mixed with an equal volume of methanol to create the alkoxide solution. The contents of the two beakers were combined and the solution was poured into a Petri dish and allowed to sit at room temperature for 15 min to allow for sol-gel formation. Methanol was added to cover the gel and replaced every 24 hours for a total period of 4 days. The gel was then washed with 20 mM Tris-HCl pH 7.5 for 72 hours as above, except that the solution was changed every 12 hours.

Figure 12:
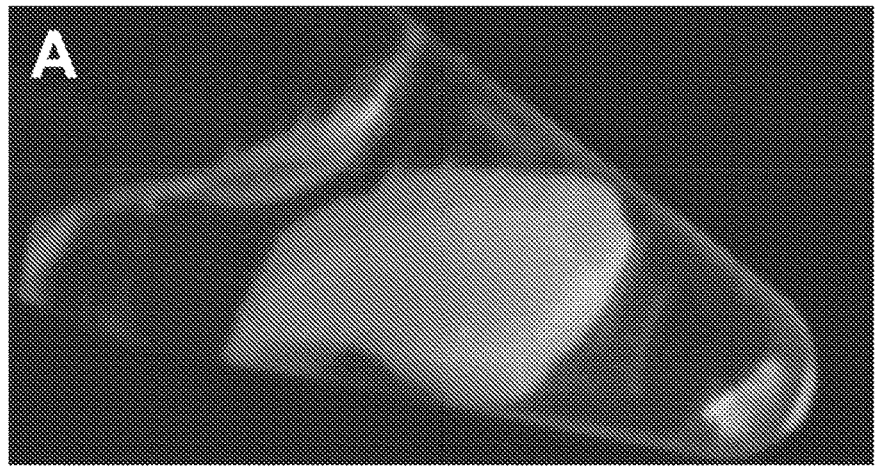
FIG. 12A is an image of GFPmut2-Car9 immobilized onto and within a silica sol-gel after storage at 4° C. for 2 months.
FIG. 12B is an image of the sol-gel of FIG. 12A after incubation for 48 hours at 4° C. with 0.5M arginine.
Figure 12:
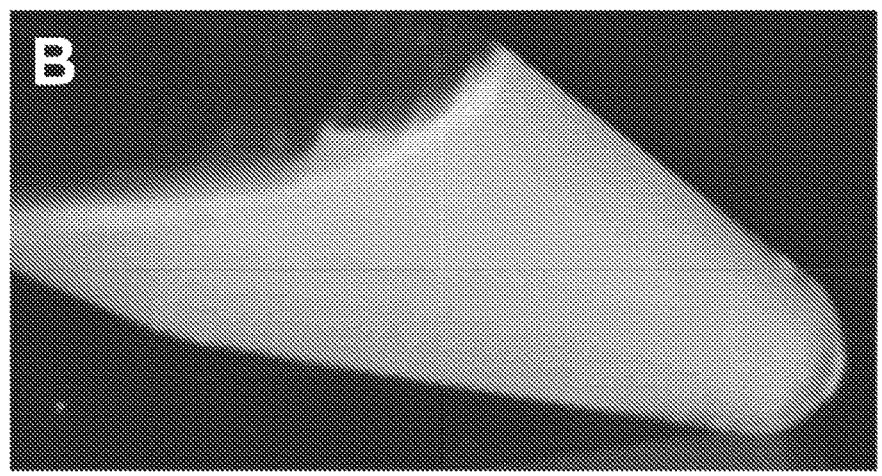

For protein immobilization, the gel was broken into pieces and a ~1 cm$^3$ piece was immersed into 1 mL of clarified lysate from induced SF100(pGFPmut2-Car9) cultures and incubated overnight at 4° C. The protein-loaded gel was then placed into 10 mL of 20 mM Tris-HCl at pH 7.5, allowed to sit for 10 minutes, and washed 5 times until all fluorescence had disappeared from the liquid (FIG. 12A). The hydrated gel could be stored for over two months at 4° C. without any detectable decrease of fluorescence or leaching of GFP into the buffer. Furthermore, the immobilized protein could be released when by immersing the gel in 1 mL of 20 mM Tris-HCl at pH 7.5 buffer supplemented with 0.5M arginine (FIG. 12B).

These data indicate that the Car9 affinity tag enables efficient immobilization of proteins with silica networks prepared by sol-gel processes, and that the stably entrapped protein can be chemically released in an active form by chemical treatment.

Further Examples

1. A protein comprising SEQ ID NO.: 1.
2. A protein comprising SEQ ID NO.: 2.
3. A protein comprising SEQ ID NO.: 3.
4. A protein comprising SEQ ID NO.: 4.

5. A protein comprising an amino acid sequence having a homology of at least 70%, at least 80%, at least 90%, or at least 95% with the amino acid sequence of any one of SEQ ID NOs.: 1 to 4.

6. The protein of any one of examples 1 to 5, wherein the protein is a fusion protein.

7. The protein of example 6, wherein the fusion protein comprises a polyclonal antibody, a monoclonal antibody, a complement determining region-grafted antibody preparation, a hybrid antibody, an altered antibody, a F(ab)'$_2$ fragment, a Fab molecule, a Fv fragment, a single domain antibody, a chimeric antibody, or a fragment thereof.

8. A substrate comprising a bound protein of any one of examples 1 to 4.

9. The substrate of example 8, wherein the substrate includes a surface comprising a silicon oxide.

10. The substrate of example 8 or example 9, wherein the substrate comprises silica.

11. A method of isolating a protein, the method comprising:
    contacting a silicon oxide substrate with a fluid comprising the protein for a time sufficient to allow the protein to bind to the silicon oxide substrate;
    contacting the silicon oxide substrate with a washing fluid; and
    contacting the silicon oxide substrate with a releasing agent to release the bound protein.

12. The method of example 11, wherein the protein is a protein of any one of examples 1 to 7.

13. The method of example 11 or example 12, wherein the releasing agent comprises lysine and/or arginine.

14. The method of example 11 or example 12, wherein the releasing agent comprises a protease.

15. The method of any one of examples 11 to 14, wherein the silicon oxide substrate comprises silica, borosilicate, controlled pore glass, quartz, and/or oxidized silicon.

16. The method of any one of examples 12 to 13, further comprising contacting the released protein with a protease to cleave the SEQ ID NOs.: 1 to 4, or homologous portion thereof, from the protein.

17. A kit for purifying the protein of any one of examples 1 to 7, the kit comprising:
    a silicon oxide substrate;
    a vessel for retainably holding the silicon oxide substrate;
    a receptacle for receiving eluent passing through the vessel; and
    a releasing agent.

18. The kit of example 17 further comprising instructions for using the kit to purify the protein.

19. The kit of example 17 or example 18, wherein the releasing agent comprises arginine and/or lysine.

20. The kit of example 17 or example 18, wherein the releasing agent comprises a protease 21. A nucleic acid encoding the protein of any one of examples 1 to 7.

22. A recombinant expression vector comprising the nucleic acid of example 21.

23. A host cell transfected with the recombinant expression vector of example 22.

24. A silica sol-gel comprising a protein comprising any one of SEQ ID NOs.: 1 to 4.

25. The silica sol-gel of example 24, wherein the protein is a fusion protein.

26. The silica sol-gel of example 23 or example 24, wherein the protein elutes from the silica sol-gel in the presence of a solution comprising arginine and/or lysine.

27. The silica sol-gel of example 26, wherein the solution comprises arginine and/or lysine in a concentration of at least about 0.1M.

Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2nd Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the *Ambion* 1998 *Catalog* (Ambion, Austin, Tex.). Aspects of the disclosure can be modified, if necessary, to employ the systems, functions, and concepts of the above references and application to provide yet further embodiments of the disclosure. These and other changes can be made to the disclosure in light of the detailed description.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

As used throughout the present application, the term "polypeptide" is used in its broadest sense to refer to a sequence of subunit amino acids. The polypeptides of the invention may comprise L-amino acids, D-amino acids (which are resistant to L-amino acid-specific proteases in vivo), or a combination of D- and L-amino acids. The polypeptides described herein may be chemically synthesized or recombinantly expressed.

From the foregoing, it will be appreciated that specific embodiments of the invention have been described herein for purposes of illustration, but well-known structures and functions have not been shown or described in detail to avoid unnecessarily obscuring the description of the embodiments of the technology. Where the context permits, singular or plural terms may also include the plural or singular term, respectively. For example, as used herein, the singular forms "a", "an" and "the" include plural referents unless the context clearly dictates otherwise. "And" as used herein is interchangeably used with "or" unless expressly stated otherwise. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the words "herein," "above," and "below" and words of similar import, when used in this application, shall refer to this application as a whole and not to any particular portions of the application. The term "comprising" is used throughout to mean including at least the recited feature(s) such that any greater number of the same feature and/or additional types of other features are not precluded.

It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A protein comprising a sequence having at least 75% sequence identity to SEQ. ID. NO: 1, wherein the protein is bound to a silicon oxide substrate.

2. A substrate comprising a protein bound to a silicon oxide substrate, the protein comprising an amino acid sequence having at least 75% sequence identity to the amino acid sequence of SEQ ID NO: 1.

3. The substrate of claim 2 wherein the bound protein has an amino acid sequence having at least 80%, at least 90% or at least 95% sequence identity to the amino acid sequence of SEQ. ID. NO: 1.

4. The substrate of claim 2, wherein the bound protein is a portion of a fusion protein.

5. The substrate of claim 4, wherein the fusion protein comprises a polyclonal antibody, a monoclonal antibody, a complement determining region-grafted antibody preparation, a hybrid antibody, an altered antibody, a F(ab)'$_2$ fragment, a Fab molecule, a Fv fragment, a single domain antibody, a chimeric antibody, or a fragment thereof.

6. The substrate of claim 2, wherein the substrate comprises silica.

7. A kit for purifying a protein comprising an amino acid sequence having at least 75% sequence identity to the amino acid sequence of SEQ. ID. NO:1, the kit comprising;
   a silicon oxide substrate that binds to the protein;
   a vessel for retainably holding the silicon oxide substrate;
   a receptacle for receiving eluent passing through the vessel; and
   a releasing agent.

8. The kit of claim 7 further comprising instructions for using the kit to purify the protein.

9. The kit of claim 7, wherein the releasing agent comprises arginine and/or lysine.

10. The kit of claim 7, wherein the releasing agent comprises a protease.

11. A method of isolating a protein comprising an amino acid sequence having at least 75% sequence identity to the amino acid sequence of SEQ. ID. NO: 1, the method comprising:

contacting a silicon oxide substrate with a fluid comprising the protein for a time sufficient to allow the protein to bind to the silicon oxide substrate;

contacting the silicon oxide substrate with a washing fluid; and contacting the silicon oxide substrate with a releasing agent to release the bound protein.

12. The method of claim 11, wherein the releasing agent comprises lysine and/or arginine.

13. The method of claim 11, wherein the releasing agent comprises a protease.

14. The method of claim 11, wherein the silicon oxide substrate comprises silica, borosilicate, controlled pore glass, quartz, and/or oxidized silicon.

15. The method of claim 11, further comprising contacting the released protein with a protease to cleave the SEQ ID NO.: 1 from the released protein.

* * * * *

SEQUENCE LISTING

```
<160> NUMBER OF SEQ ID NOS: 19

<210> SEQ ID NO 1
<211> LENGTH: 12
<212> TYPE: PRT
<213> ORGANISM: Artificial sequence
<220> FEATURE:
<223> OTHER INFORMATION: Synthesized

<400> SEQUENCE: 1

Asp Ser Ala Arg Gly Phe Lys Lys Pro Gly Lys Arg
1               5                   10

<210> SEQ ID NO 2
<211> LENGTH: 12
<212> TYPE: PRT
<213> ORGANISM: Artificial sequence
<220> FEATURE:
<223> OTHER INFORMATION: Synthesized

<400> SEQUENCE: 2

Lys Lys Arg Ser Pro Ile Leu Ala Ser Lys Arg Arg
1               5                   10

<210> SEQ ID NO 3
<211> LENGTH: 12
<212> TYPE: PRT
<213> ORGANISM: Artificial sequence
<220> FEATURE:
<223> OTHER INFORMATION: Synthesized

<400> SEQUENCE: 3

Arg Asp Arg Gly Ala Thr Tyr Pro Lys Leu Gly Arg
1               5                   10

<210> SEQ ID NO 4
<211> LENGTH: 12
<212> TYPE: PRT
<213> ORGANISM: Artificial sequence
<220> FEATURE:
<223> OTHER INFORMATION: Synthesized

<400> SEQUENCE: 4

Arg Asn Lys Arg Cys Ser Ser Lys Thr Arg Arg Gly
1               5                   10

<210> SEQ ID NO 5
<211> LENGTH: 12
<212> TYPE: PRT
<213> ORGANISM: Artificial sequence
<220> FEATURE:
<223> OTHER INFORMATION: Synthesized

<400> SEQUENCE: 5
```

Arg Thr Tyr Leu Pro Leu Pro Trp Met Ala Ala Leu
1               5                   10

<210> SEQ ID NO 6
<211> LENGTH: 123
<212> TYPE: PRT
<213> ORGANISM: Artificial sequence
<220> FEATURE:
<223> OTHER INFORMATION: Synthesized

<400> SEQUENCE: 6

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Asp Ser Ala Arg Gly Phe Lys Lys Pro Gly Lys Arg Gly
            35                  40                  45

Cys Pro Lys Met Ile Ala Pro Ile Leu Asp Glu Ile Ala Asp Glu Tyr
        50                  55                  60

Gln Gly Lys Leu Thr Val Ala Lys Leu Asn Ile Asp Gln Asn Pro Gly
65                  70                  75                  80

Thr Ala Pro Lys Tyr Gly Ile Arg Gly Ile Pro Thr Leu Leu Leu Phe
                85                  90                  95

Lys Asn Gly Glu Val Ala Ala Thr Lys Val Gly Ala Leu Ser Lys Gly
            100                 105                 110

Gln Leu Lys Glu Phe Leu Asp Ala Asn Leu Ala
        115                 120

<210> SEQ ID NO 7
<211> LENGTH: 109
<212> TYPE: PRT
<213> ORGANISM: Escherichia coli

<400> SEQUENCE: 7

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala
            100                 105

<210> SEQ ID NO 8
<211> LENGTH: 5308
<212> TYPE: DNA
<213> ORGANISM: Artificial sequence
<220> FEATURE:
<223> OTHER INFORMATION: Synthesized

<400> SEQUENCE: 8
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120

```
ctttctcgcc acgttcgccg gctttccccg tcaagctcta aatcggggc tccctttagg      180
gttccgattt agtgctttac ggcacctcga ccccaaaaaa cttgattagg gtgatggttc      240
acgtagtggg ccatcgccct gatagacggt ttttcgccct ttgacgttgg agtccacgtt      300
ctttaatagt ggactcttgt tccaaactgg aacaacactc aaccctatct cggtctattc      360
ttttgattta aagggatttt tgccgatttc ggcctattgg ttaaaaaatg agctgattta      420
acaaaatttt aacgcgaatt ttaacaaaat attaacgttt acaatttcag gtggcacttt      480
tcggggaaat gtgcgcggaa cccctatttg tttattttc taaatacatt caaatatgta       540
tccgctcatg aattaattct tagaaaaact catcgagcat caaatgaaac tgcaatttat       600
tcatatcagg attatcaata ccatattttt gaaaaagccg tttctgtaat gaaggagaaa      660
actcaccgag gcagttccat aggatggcaa gatcctggta tcggtctgcg attccgactc      720
gtccaacatc aatacaacct attaatttcc cctcgtcaaa aataaggtta tcaagtgaga      780
aatcaccatg agtgacgact gaatccggtg agaatggcaa aagtttatgc atttctttcc      840
agacttgttc aacaggccag ccattacgct cgtcatcaaa atcactcgca tcaaccaaac      900
cgttattcat tcgtgattgc gcctgagcga cgaaatac gcgatcgctg ttaaaaggac         960
aattacaaac aggaatcgaa tgcaaccggc gcaggaacac tgccagcgca tcaacaatat     1020
ttcacctga atcaggatat tcttctaata cctggaatgc tgttttcccg gggatcgcag        1080
tggtgagtaa ccatgcatca tcaggagtac ggataaaatg cttgatggtc ggaagaggca     1140
taaattccgt cagccagttt agtctgacca tctcatctgt aacatcattg gcaacgctac     1200
ctttgccatg tttcagaaac aactctggcg catcgggctt cccatacaat cgatagattg     1260
tcgcacctga ttgcccgaca ttatcgcgag cccatttata cccatataaa tcagcatcca     1320
tgttggaatt taatcgcggc ctagagcaag acgtttcccg ttgaatatgg ctcataacac     1380
cccttgtatt actgtttatg taagcagaca gttttattgt tcatgaccaa aatcccttaa     1440
cgtgagtttt cgttccactg agcgtcagac cccgtagaaa agatcaaagg atcttcttga     1500
gatccttttt ttctgcgcgt aatctgctgc ttgcaaacaa aaaaaccacc gctaccagcg     1560
gtggtttgtt tgccggatca agagctacca actctttttc cgaaggtaac tggcttcagc     1620
agagcgcaga taccaaatac tgtccttcta gtgtagccgt agttaggcca ccacttcaag     1680
aactctgtag caccgcctac atacctcgct ctgctaatcc tgttaccagt ggctgctgcc     1740
agtggcgata agtcgtgtct taccgggttg gactcaagac gatagttacc ggataaggcg     1800
cagcggtcgg gctgaacggg gggttcgtgc acacagccca gcttggagcg aacgacctac     1860
accgaactga gatacctaca gcgtgagcta tgagaaagcg ccacgcttcc cgaagggaga     1920
aaggcggaca ggtatccggt aagcggcagg gtcggaacag gagagcgcac gagggagctt     1980
ccagggggaa acgcctggta tctttatagt cctgtcgggt ttcgccacct ctgacttgag     2040
cgtcgatttt tgtgatgctc gtcagggggg cggagcctat ggaaaaacgc cagcaacgcg     2100
gcctttttac ggttcctggc cttttgctgg ccttttgctc acatgttctt tcctgcgtta     2160
tcccctgatt ctgtggataa ccgtattacc gcctttgagt gagctgatac cgctcgccgc     2220
agccgaacga ccgagcgcag cgagtcagtg agcgaggaag cggaagagcg cctgatgcgg     2280
tattttctcc ttacgcatct gtgcggtatt tcacaccgca tatatggtgc actctcagta     2340
caatctgctc tgatgccgca tagttaagcc agtatacact ccgctatcgc tacgtgactg     2400
ggtcatggct gcgccccgac acccgccaac acccgctgac gcgccctgac gggcttgtct     2460
```

```
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacaattatg acaacttgac ggctacatca ttcactttt    3780 cttcacaacc ggcacggaac tcgctcgggc tggccccgt gcatttttta aatacccgcg    3840
agaaatagag ttgatcgtca aaaccaacat tgcgaccgac ggtggcgata ggcatccggg    3900
tggtgctcaa aagcagcttc gcctggctga tacgttggtc ctcgcgccag cttaagacgc    3960
taatccctaa ctgctggcgg aaaagatgtg acagacgcga cggcgacaag caaacatgct    4020
gtgcgacgct ggcgatatca aaattgctgt ctgccaggtg atcgctgatg tactgacaag    4080
cctcgcgtac ccgattatcc atcggtggat ggagcgactc gttaatcgct tccatgcgcc    4140
gcagtaacaa ttgctcaagc agatttatcg ccagcagctc cgaatagcgc ccttcccctt    4200
gcccggcgtt aatgatttgc ccaaacaggt cgctgaaatg cggctggtgc gcttcatccg    4260
ggcgaaagaa ccccgtattg gcaaatattg acggccagtt aagccattca tgccagtagg    4320
cgcgcggacg aaagtaaacc cactggtgat accattcgcg agcctccgga tgacgaccgt    4380
agtgatgaat ctctcctggc gggaacagca aaatatcacc cggtcggcaa acaaattctc    4440
gtccctgatt tttcaccacc ccctgaccgc gaatggtgag attgagaata taccctttca    4500
ttcccagcgg tcggtcgata aaaaaatcga gataaccgtt ggcctcaatc ggcgttaaac    4560
ccgccaccag atgggcatta acgagtatc ccggcagcag gggatcattt tgcgcttcag    4620
ccatactttt catactcccg ccattcagag aagaaaccaa ttgtccatat tgcatcagac    4680
attgccgtca ctgcgtcttt tactggctct tctcgctaac caaaccggta accccgctta    4740
ttaaaagcat tctgtaacaa agcgggacca aagccatgac aaaaacgcgt aacaaaagtg    4800
tctataatca cggcagaaaa gtccacattg attatttgca cggcgtcaca ctttgctatg    4860
```

```
ccatagcatt tttatccata agattagcgg atcctacctg acgcttttta tcgcaactct   4920
ctactgtttc tccatacccg ttttttlggg ctagcgaatt cgagctcggt acccggggat   4980
cctctagaaa taattttgtt taactttaag aaggagatat acatatggct agcatgactg   5040
gtggacagca aatgggtcgc ggatccgaat tcgagctccg tcgacaagct tggcggcggc   5100
tctgacagtg ctcgcgggtt taaaaagcct gggaagcggt aataactcga gcaccaccac   5160
caccaccact gagatccggc tgctaacaaa gcccgaaagg aagctgagtt ggctgctgcc   5220
accgctgagc aataactagc ataaccccttt ggggcctcta acgggtcttt gaggggtttt   5280
ttgctgaaag gaggaactat atccggat                                     5308
```

<210> SEQ ID NO 9  
<211> LENGTH: 238  
<212> TYPE: PRT  
<213> ORGANISM: Escherichia coli

<400> SEQUENCE: 9

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ala Tyr Gly Leu Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 10  
<211> LENGTH: 256  
<212> TYPE: PRT  
<213> ORGANISM: Artificial sequence  
<220> FEATURE:  
<223> OTHER INFORMATION: Synthesized

<400> SEQUENCE: 10

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
50                  55                  60

Ala Tyr Gly Leu Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys Lys Leu
225                 230                 235                 240

Gly Gly Gly Ser Asp Ser Ala Arg Gly Phe Lys Lys Pro Gly Lys Arg
                245                 250                 255

<210> SEQ ID NO 11
<211> LENGTH: 388
<212> TYPE: PRT
<213> ORGANISM: Artificial sequence
<220> FEATURE:
<223> OTHER INFORMATION: Synthesized

<400> SEQUENCE: 11

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110
```

```
Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
            355                 360                 365

Ser Ser Lys Leu Gly Gly Gly Ser Asp Ser Ala Arg Gly Phe Lys Lys
            370                 375                 380

Pro Gly Lys Arg
385

<210> SEQ ID NO 12
<211> LENGTH: 274
<212> TYPE: PRT
<213> ORGANISM: Artificial sequence
<220> FEATURE:
<223> OTHER INFORMATION: Synthesized

<400> SEQUENCE: 12

Met Gly Ser Ser His His His His His His Ser Ser Gly Leu Val Pro
1               5                   10                  15

Arg Gly Ser His Met Val Ser Lys Gly Glu Glu Asp Asn Met Ala Ile
            20                  25                  30

Ile Lys Glu Phe Met Arg Phe Lys Val His Met Glu Gly Ser Val Asn
        35                  40                  45

Gly His Glu Phe Glu Ile Glu Gly Glu Gly Glu Gly Arg Pro Tyr Glu
    50                  55                  60

Gly Thr Gln Thr Ala Lys Leu Lys Val Thr Lys Gly Gly Pro Leu Pro
65                  70                  75                  80
```

```
Phe Ala Trp Asp Ile Leu Ser Pro Gln Phe Met Tyr Gly Ser Lys Ala
                85                  90                  95

Tyr Val Lys His Pro Ala Asp Ile Pro Asp Tyr Leu Lys Leu Ser Phe
            100                 105                 110

Pro Glu Gly Phe Lys Trp Glu Arg Val Met Asn Phe Glu Asp Gly Gly
        115                 120                 125

Val Val Thr Val Thr Gln Asp Ser Ser Leu Gln Asp Gly Glu Phe Ile
130                 135                 140

Tyr Lys Val Lys Leu Arg Gly Thr Asn Phe Pro Ser Asp Gly Pro Val
145                 150                 155                 160

Met Gln Lys Lys Thr Met Gly Trp Glu Ala Ser Ser Glu Arg Met Tyr
                165                 170                 175

Pro Glu Asp Gly Ala Leu Lys Gly Glu Ile Lys Gln Arg Leu Lys Leu
            180                 185                 190

Lys Asp Gly Gly His Tyr Asp Ala Glu Val Lys Thr Thr Tyr Lys Ala
        195                 200                 205

Lys Lys Pro Val Gln Leu Pro Gly Ala Tyr Asn Val Asn Ile Lys Leu
210                 215                 220

Asp Ile Thr Ser His Asn Glu Asp Tyr Thr Ile Val Glu Gln Tyr Glu
225                 230                 235                 240

Arg Ala Glu Gly Arg His Ser Thr Gly Gly Met Asp Glu Leu Tyr Lys
                245                 250                 255

Lys Leu Gly Gly Gly Ser Asp Ser Ala Arg Gly Phe Lys Lys Pro Gly
            260                 265                 270

Lys Arg

<210> SEQ ID NO 13
<211> LENGTH: 3607
<212> TYPE: DNA
<213> ORGANISM: Artificial sequence
<220> FEATURE:
<223> OTHER INFORMATION: Synthesized

<400> SEQUENCE: 13
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg  cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt caataaatgt gtacttaaga   420
ccagcagtag tgatgaagtt atagtttttct ataccctgctc cattttttgct gtagtctgaa   480 gtgttattat tgtgatcata aagtgaagta ttacctttt  tattcgtaac ccgattccat    540
gcgccttcaa cataaacttt tgcgttaggt gtgacgtaat aacctgcatt gactgcaaca   600
gaatagtaat tttggtcttt gaccttactg cgataagtga ttcttttcc cgggtcatag   660 tgttcatcgt tatcagatga ttccacccag ccgctgtatt taaatgtgcc accgagttca   720
aaatcttcat aacgataact tccagtcaag ccaatgtagg gcatttttaa acgttgtttg   780
tagccgattg ctctttctcc attcgggaag gagccgatat catctctgaa tccctcctca   840
gaactgtaga tataggaacc acctctggct gtaaagctat aacggctttc ctgatatccg   900
```

```
gccatgagtc ccaggcggta attgggttcg ttgaggagcc agcctttgat attcagatca    960
aattcgttgg cataattgag ttgtgtatca gggtgtctac tttcatccgt ccaggttccg   1020
gggttactgg aatccatcca gtcctgatcg accatattgc cacctcggct gccgagagtt   1080
gtccagccag cagccccgat agatatctgg ggcatcaaat cccaattaat tgcacccttta  1140
ataattgcag cgttattgaa tttccagtcg agttgactga cttttcggcc tccttcttcg   1200
gctagataaa cacgctcttt tgttttccg ctcagagttc caagactaat gtccgcattt    1260
atgttgtcag gagtaaacga taaagtctcg gtagaagcaa aagagctgat cgcaataggg   1320
gttgtcagga ctattcccag aagtttcgcc cgcatctgca ggcatgcaag cttggcgtaa   1380
tcatggtcat agctgtttcc tgtgtgaaat tgttatccgc tcacaattcc acacaacata   1440
cgagccggaa gcataaagtg taaagcctgg ggtgcctaat gagtgagcta actcacatta   1500
attgcgttgc gctcactgcc cgctttccag tcgggaaacc tgtcgtgcca gctgcattaa   1560
tgaatcggcc aacgcgcggg gagaggcggt ttgcgtattg ggcgctcttc cgcttcctcg   1620
ctcactgact cgctgcgctc ggtcgttcgg ctgcggcgag cggtatcagc tcactcaaag   1680
gcggtaatac ggttatccac agaatcaggg gataacgcag gaaagaacat gtgagcaaaa   1740
ggccagcaaa aggccaggaa ccgtaaaaag gccgcgttgc tggcgttttt ccataggctc   1800
cgcccccctg acgagcatca caaaaatcga cgctcaagtc agaggtggcg aaacccgaca   1860
ggactataaa gataccaggc gtttccccct ggaagctccc tcgtgcgctc tcctgttccg   1920
accctgccgc ttaccggata cctgtccgcc tttctccctt cgggaagcgt ggcgctttct   1980
caatgctcac gctgtaggta tctcagttcg gtgtaggtcg ttcgctccaa gctgggctgt   2040
gtgcacgaac ccccgttca gcccgaccgc tgcgccttat ccggtaacta tcgtcttgag    2100
tccaacccgg taagacacga cttatcgcca ctggcagcag ccactggtaa caggattagc   2160
agagcgaggt atgtaggcgg tgctacagag ttcttgaagt ggtggcctaa ctacggctac   2220
actagaagga cagtatttgg tatctgcgct ctgctgaagc cagttacctt cggaaaaaga   2280
gttggtagct cttgatccgg caaacaaacc accgctggta gcggtggttt ttttgtttgc   2340
aagcagcaga ttacgcgcag aaaaaaagga tctcaagaag atcctttgat cttttctacg   2400
gggtctgacg ctcagtggaa cgaaaactca cgttaaggga ttttggtcat gagattatca   2460
aaaaggatct tcacctagat ccttttaaat taaaaatgaa gttttaaatc aatctaaagt   2520
atatatgagt aaacttggtc tgacagttac caatgcttaa tcagtgaggc acctatctca   2580
gcgatctgtc tatttcgttc atccatagtt gcctgactcc ccgtcgtgta gataactacg   2640
atacgggagg gcttaccatc tggccccagt gctgcaatga taccgcgaga cccacgctca   2700
ccggctccag atttatcagc aataaaccag ccagccggaa gggccgagcg cagaagtggt   2760
cctgcaactt tatccgcctc catccagtct attaattgtt gccgggaagc tagagtaagt   2820
agttcgccag ttaatagttt gcgcaacgtt gttgccattg ctacaggcat cgtggtgtca   2880
cgctcgtcgt ttggtatggc ttcattcagc tccggttccc aacgatcaag gcgagttaca   2940
tgatccccca tgttgtgcaa aaaagcggtt agctccttcg gtcctccgat cgttgtcaga   3000
agtaagttgg ccgcagtgtt atcactcatg gttatggcag cactgcataa ttctcttact   3060
gtcatgccat ccgtaagatg cttttctgtg actggtgagt actcaaccaa gtcattctga   3120
gaatagtgta tgcggcgacc gagttgctct tgcccggcgt caatacggga taataccgcg   3180
ccacatagca gaactttaaa agtgctcatc attggaaaac gttcttcggg gcgaaaactc   3240
tcaaggatct taccgctgtt gagatccagt tcgatgtaac ccactcgtgc acccaactga   3300
```

```
tcttcagcat cttttacttt caccagcgtt tctgggtgag caaaaacagg aaggcaaaat    3360
gccgcaaaaa agggaataag ggcgacacgg aaatgttgaa tactcatact cttccttttt    3420
caatattatt gaagcattta tcagggttat tgtctcatga gcggatacat atttgaatgt    3480
atttagaaaa ataaacaaat aggggttccg cgcacatttc cccgaaaagt gccacctgac    3540
gtctaagaaa ccattattat catgacatta acctataaaa ataggcgtat cacgaggccc    3600
tttcgtc                                                              3607
```

<210> SEQ ID NO 14
<211> LENGTH: 256
<212> TYPE: PRT
<213> ORGANISM: Artificial sequence
<220> FEATURE:
<223> OTHER INFORMATION: Synthesized

<400> SEQUENCE: 14

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ala Tyr Gly Leu Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys Lys Leu
225                 230                 235                 240

Gly Gly Gly Ser Arg Thr Tyr Leu Pro Leu Pro Trp Met Ala Ala Leu
                245                 250                 255

<210> SEQ ID NO 15
<211> LENGTH: 499
<212> TYPE: PRT
<213> ORGANISM: Artificial sequence
<220> FEATURE:
<223> OTHER INFORMATION: Synthesized

<400> SEQUENCE: 15

```
Met Ala Gln Val Ile Asn Thr Asn Ser Leu Ser Leu Ile Thr Gln Asn
1               5                   10                  15

Asn Ile Asn Lys Asn Gln Ser Ala Leu Ser Ser Ser Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ala Arg Asn Ala Asn Asp Gly Ile Ser Val Ala Gln Thr Thr Glu Gly
65                  70                  75                  80

Ala Leu Ser Glu Ile Asn Asn Leu Gln Arg Val Arg Glu Leu Thr
                85                  90                  95

Val Gln Ala Thr Thr Gly Thr Asn Ser Glu Ser Asp Leu Ser Ser Ile
                100                 105                 110

Gln Asp Glu Ile Lys Ser Arg Leu Asp Glu Ile Asp Arg Val Ser Gly
            115                 120                 125

Gln Thr Gln Phe Asn Gly Val Asn Val Leu Ala Lys Asn Gly Ser Met
130                 135                 140

Lys Ile Gln Val Gly Ala Asn Asp Asn Gln Thr Ile Thr Ile Asp Leu
145                 150                 155                 160

Lys Gln Ile Asp Ala Lys Thr Leu Gly Leu Asp Gly Phe Ser Val Lys
                165                 170                 175

Asn Asn Asp Thr Val Thr Thr Ser Ala Pro Val Thr Ala Phe Gly Ala
            180                 185                 190

Thr Thr Thr Asn Asn Ile Lys Leu Thr Gly Ile Thr Leu Ser Thr Glu
        195                 200                 205

Ala Ala Thr Asp Thr Gly Gly Thr Asn Pro Ala Ser Ile Glu Gly Val
    210                 215                 220

Tyr Thr Asp Asn Gly Asn Asp Tyr Tyr Ala Lys Ile Thr Gly Gly Asp
225                 230                 235                 240

Asn Asp Met Ser Asp Lys Ile Ile His Leu Thr Asp Asp Ser Phe Asp
                245                 250                 255

Thr Asp Val Leu Lys Ala Asp Gly Ala Ile Leu Val Asp Phe Trp Ala
            260                 265                 270

Glu Trp Cys Gly Pro Cys Lys Met Ile Ala Pro Ile Leu Asp Glu Ile
        275                 280                 285

Ala Asp Glu Tyr Gln Gly Lys Leu Thr Val Ala Lys Leu Asn Ile Asp
    290                 295                 300

Gln Asn Pro Gly Thr Ala Pro Lys Tyr Gly Ile Arg Gly Ile Pro Thr
305                 310                 315                 320

Leu Leu Leu Phe Lys Asn Gly Glu Val Ala Ala Thr Lys Val Gly Ala
                325                 330                 335

Leu Ser Lys Gly Gln Leu Lys Glu Phe Leu Asp Ala Asn Leu Ala Cys
            340                 345                 350

Ala Ala Ser Ser Pro Thr Ala Val Lys Leu Gly Gly Asp Asp Gly Lys
        355                 360                 365

Thr Glu Val Val Asp Ile Asp Gly Lys Thr Tyr Asp Ser Ala Asp Leu
    370                 375                 380

Asn Gly Gly Asn Leu Gln Thr Gly Leu Thr Ala Gly Gly Glu Ala Leu
385                 390                 395                 400

Thr Ala Val Ala Asn Gly Lys Thr Thr Asp Pro Leu Lys Ala Leu Asp
                405                 410                 415
```

```
Asp Ala Ile Ala Ser Val Asp Lys Phe Arg Ser Ser Leu Gly Ala Val
            420                 425                 430

Gln Asn Arg Leu Asp Ser Ala Val Thr Asn Leu Asn Thr Thr Thr
            435                 440                 445

Asn Leu Ser Glu Ala Gln Ser Arg Ile Gln Asp Ala Asp Tyr Ala Thr
450                 455                 460

Glu Val Ser Asn Met Ser Lys Ala Gln Ile Ile Gln Gln Ala Gly Asn
465                 470                 475                 480

Ser Val Leu Ala Lys Ala Asn Gln Val Pro Gln Gln Val Leu Ser Leu
                485                 490                 495

Leu Gln Gly

<210> SEQ ID NO 16
<211> LENGTH: 513
<212> TYPE: PRT
<213> ORGANISM: Artificial sequence
<220> FEATURE:
<223> OTHER INFORMATION: Synthesized

<400> SEQUENCE: 16

Met Ala Gln Val Ile Asn Thr Asn Ser Leu Ser Leu Ile Thr Gln Asn
1               5                   10                  15

Asn Ile Asn Lys Asn Gln Ser Ala Leu Ser Ser Ser Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ala Arg Asn Ala Asn Asp Gly Ile Ser Val Ala Gln Thr Thr Glu Gly
65                  70                  75                  80

Ala Leu Ser Glu Ile Asn Asn Asn Leu Gln Arg Val Arg Glu Leu Thr
                85                  90                  95

Val Gln Ala Thr Thr Gly Thr Asn Ser Glu Ser Asp Leu Ser Ser Ile
            100                 105                 110

Gln Asp Glu Ile Lys Ser Arg Leu Asp Glu Ile Asp Arg Val Ser Gly
        115                 120                 125

Gln Thr Gln Phe Asn Gly Val Asn Val Leu Ala Lys Asn Gly Ser Met
    130                 135                 140

Lys Ile Gln Val Gly Ala Asn Asp Asn Gln Thr Ile Thr Ile Asp Leu
145                 150                 155                 160

Lys Gln Ile Asp Ala Lys Thr Leu Gly Leu Asp Gly Phe Ser Val Lys
                165                 170                 175

Asn Asn Asp Thr Val Thr Thr Ser Ala Pro Val Thr Ala Phe Gly Ala
            180                 185                 190

Thr Thr Thr Asn Asn Ile Lys Leu Thr Gly Ile Thr Leu Ser Thr Glu
        195                 200                 205

Ala Ala Thr Asp Thr Gly Gly Thr Asn Pro Ala Ser Ile Glu Gly Val
    210                 215                 220

Tyr Thr Asp Asn Gly Asn Asp Tyr Tyr Ala Lys Ile Thr Gly Gly Asp
225                 230                 235                 240

Asn Asp Met Ser Asp Lys Ile Ile His Leu Thr Asp Asp Ser Phe Asp
                245                 250                 255

Thr Asp Val Leu Lys Ala Asp Gly Ala Ile Leu Val Asp Phe Trp Ala
            260                 265                 270
```

```
Glu Trp Cys Gly Pro Lys Lys Arg Ser Pro Ile Leu Ala Ser Lys Arg
            275                 280                 285

Arg Gly Pro Cys Lys Met Ile Ala Pro Ile Leu Asp Glu Ile Ala Asp
        290                 295                 300

Glu Tyr Gln Gly Lys Leu Thr Val Ala Lys Leu Asn Ile Asp Gln Asn
305                 310                 315                 320

Pro Gly Thr Ala Pro Lys Tyr Gly Ile Arg Gly Ile Pro Thr Leu Leu
                325                 330                 335

Leu Phe Lys Asn Gly Glu Val Ala Ala Thr Lys Val Gly Ala Leu Ser
            340                 345                 350

Lys Gly Gln Leu Lys Glu Phe Leu Asp Ala Asn Leu Ala Cys Ala Ala
        355                 360                 365

Ser Ser Pro Thr Ala Val Lys Leu Gly Gly Asp Asp Gly Lys Thr Glu
    370                 375                 380

Val Val Asp Ile Asp Gly Lys Thr Tyr Asp Ser Ala Asp Leu Asn Gly
385                 390                 395                 400

Gly Asn Leu Gln Thr Gly Leu Thr Ala Gly Glu Ala Leu Thr Ala
                405                 410                 415

Val Ala Asn Gly Lys Thr Thr Asp Pro Leu Lys Ala Leu Asp Asp Ala
            420                 425                 430

Ile Ala Ser Val Asp Lys Phe Arg Ser Ser Leu Gly Ala Val Gln Asn
        435                 440                 445

Arg Leu Asp Ser Ala Val Thr Asn Leu Asn Asn Thr Thr Asn Leu
    450                 455                 460

Ser Glu Ala Gln Ser Arg Ile Gln Asp Ala Asp Tyr Ala Thr Glu Val
465                 470                 475                 480

Ser Asn Met Ser Lys Ala Gln Ile Ile Gln Gln Ala Gly Asn Ser Val
                485                 490                 495

Leu Ala Lys Ala Asn Gln Val Pro Gln Gln Val Leu Ser Leu Leu Gln
            500                 505                 510

Gly

<210> SEQ ID NO 17
<211> LENGTH: 513
<212> TYPE: PRT
<213> ORGANISM: Artificial sequence
<220> FEATURE:
<223> OTHER INFORMATION: Synthesized

<400> SEQUENCE: 17

Met Ala Gln Val Ile Asn Thr Asn Ser Leu Ser Leu Ile Thr Gln Asn
1               5                   10                  15

Asn Ile Asn Lys Asn Gln Ser Ala Leu Ser Ser Ser Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ala Arg Asn Ala Asn Asp Gly Ile Ser Val Ala Gln Thr Thr Glu Gly
65                  70                  75                  80

Ala Leu Ser Glu Ile Asn Asn Leu Gln Arg Val Arg Glu Leu Thr
                85                  90                  95

Val Gln Ala Thr Thr Gly Thr Asn Ser Glu Ser Asp Leu Ser Ser Ile
            100                 105                 110

Gln Asp Glu Ile Lys Ser Arg Leu Asp Glu Ile Asp Arg Val Ser Gly
```

```
                115                 120                 125
Gln Thr Gln Phe Asn Gly Val Asn Val Leu Ala Lys Asn Gly Ser Met
130                 135                 140
Lys Ile Gln Val Gly Ala Asn Asp Asn Gln Thr Ile Thr Ile Asp Leu
145                 150                 155                 160
Lys Gln Ile Asp Ala Lys Thr Leu Gly Leu Asp Gly Phe Ser Val Lys
                165                 170                 175
Asn Asn Asp Thr Val Thr Thr Ser Ala Pro Val Thr Ala Phe Gly Ala
                180                 185                 190
Thr Thr Thr Asn Asn Ile Lys Leu Thr Gly Ile Thr Leu Ser Thr Glu
                195                 200                 205
Ala Ala Thr Asp Thr Gly Gly Thr Asn Pro Ala Ser Ile Glu Gly Val
        210                 215                 220
Tyr Thr Asp Asn Gly Asn Asp Tyr Tyr Ala Lys Ile Thr Gly Gly Asp
225                 230                 235                 240
Asn Asp Met Ser Asp Lys Ile Ile His Leu Thr Asp Asp Ser Phe Asp
                245                 250                 255
Thr Asp Val Leu Lys Ala Asp Gly Ala Ile Leu Val Asp Phe Trp Ala
            260                 265                 270
Glu Trp Cys Gly Pro Asp Ser Ala Arg Gly Phe Lys Lys Pro Gly Lys
            275                 280                 285
Arg Gly Pro Cys Lys Met Ile Ala Pro Ile Leu Asp Glu Ile Ala Asp
        290                 295                 300
Glu Tyr Gln Gly Lys Leu Thr Val Ala Lys Leu Asn Ile Asp Gln Asn
305                 310                 315                 320
Pro Gly Thr Ala Pro Lys Tyr Gly Ile Arg Gly Ile Pro Thr Leu Leu
                325                 330                 335
Leu Phe Lys Asn Gly Glu Val Ala Ala Thr Lys Val Gly Ala Leu Ser
                340                 345                 350
Lys Gly Gln Leu Lys Glu Phe Leu Asp Ala Asn Leu Ala Cys Ala Ala
            355                 360                 365
Ser Ser Pro Thr Ala Val Lys Leu Gly Gly Asp Asp Gly Lys Thr Glu
        370                 375                 380
Val Val Asp Ile Asp Gly Lys Thr Tyr Asp Ser Ala Asp Leu Asn Gly
385                 390                 395                 400
Gly Asn Leu Gln Thr Gly Leu Thr Ala Gly Glu Ala Leu Thr Ala
                405                 410                 415
Val Ala Asn Gly Lys Thr Thr Asp Pro Leu Lys Ala Leu Asp Asp Ala
            420                 425                 430
Ile Ala Ser Val Asp Lys Phe Arg Ser Ser Leu Gly Ala Val Gln Asn
            435                 440                 445
Arg Leu Asp Ser Ala Val Thr Asn Leu Asn Asn Thr Thr Asn Leu
        450                 455                 460
Ser Glu Ala Gln Ser Arg Ile Gln Asp Ala Asp Tyr Ala Thr Glu Val
465                 470                 475                 480
Ser Asn Met Ser Lys Ala Gln Ile Ile Gln Gln Ala Gly Asn Ser Val
                485                 490                 495
Leu Ala Lys Ala Asn Gln Val Pro Gln Gln Val Leu Ser Leu Leu Gln
            500                 505                 510
Gly
```

<210> SEQ ID NO 18
<211> LENGTH: 513

```
<212> TYPE: PRT
<213> ORGANISM: Artificial sequence
<220> FEATURE:
<223> OTHER INFORMATION: Synthesized

<400> SEQUENCE: 18

Met Ala Gln Val Ile Asn Thr Asn Ser Leu Ser Leu Ile Thr Gln Asn
 1               5                  10                  15

Asn Ile Asn Lys Asn Gln Ser Ala Leu Ser Ser Ser Ile Glu Arg Leu
             20                  25                  30

Ser Ser Gly Leu Arg Ile Asn Ser Ala Lys Asp Asp Ala Ala Gly Gln
         35                  40                  45

Ala Ile Ala Asn Arg Phe Thr Ser Asn Ile Lys Gly Leu Thr Gln Ala
     50                  55                  60

Ala Arg Asn Ala Asn Asp Gly Ile Ser Val Ala Gln Thr Thr Glu Gly
 65                  70                  75                  80

Ala Leu Ser Glu Ile Asn Asn Asn Leu Gln Arg Val Arg Glu Leu Thr
                 85                  90                  95

Val Gln Ala Thr Thr Gly Thr Asn Ser Glu Ser Asp Leu Ser Ser Ile
            100                 105                 110

Gln Asp Glu Ile Lys Ser Arg Leu Asp Glu Ile Asp Arg Val Ser Gly
        115                 120                 125

Gln Thr Gln Phe Asn Gly Val Asn Val Leu Ala Lys Asn Gly Ser Met
    130                 135                 140

Lys Ile Gln Val Gly Ala Asn Asp Asn Gln Thr Ile Thr Ile Asp Leu
145                 150                 155                 160

Lys Gln Ile Asp Ala Lys Thr Leu Gly Leu Asp Gly Phe Ser Val Lys
                165                 170                 175

Asn Asn Asp Thr Val Thr Thr Ser Ala Pro Val Thr Ala Phe Gly Ala
            180                 185                 190

Thr Thr Thr Asn Asn Ile Lys Leu Thr Gly Ile Thr Leu Ser Thr Glu
        195                 200                 205

Ala Ala Thr Asp Thr Gly Gly Thr Asn Pro Ala Ser Ile Glu Gly Val
    210                 215                 220

Tyr Thr Asp Asn Gly Asn Asp Tyr Tyr Ala Lys Ile Thr Gly Gly Asp
225                 230                 235                 240

Asn Asp Met Ser Asp Lys Ile Ile His Leu Thr Asp Asp Ser Phe Asp
                245                 250                 255

Thr Asp Val Leu Lys Ala Asp Gly Ala Ile Leu Val Asp Phe Trp Ala
            260                 265                 270

Glu Trp Cys Gly Pro Arg Asp Arg Gly Ala Thr Tyr Pro Lys Leu Gly
        275                 280                 285

Arg Gly Pro Cys Lys Met Ile Ala Pro Ile Leu Asp Glu Ile Ala Asp
    290                 295                 300

Glu Tyr Gln Gly Lys Leu Thr Val Ala Lys Leu Asn Ile Asp Gln Asn
305                 310                 315                 320

Pro Gly Thr Ala Pro Lys Tyr Gly Ile Arg Gly Ile Pro Thr Leu Leu
                325                 330                 335

Leu Phe Lys Asn Gly Glu Val Ala Ala Thr Lys Val Gly Ala Leu Ser
            340                 345                 350

Lys Gly Gln Leu Lys Glu Phe Leu Asp Ala Asn Leu Ala Cys Ala Ala
        355                 360                 365

Ser Ser Pro Thr Ala Val Lys Leu Gly Gly Asp Gly Lys Thr Glu
    370                 375                 380
```

-continued

```
Val Val Asp Ile Asp Gly Lys Thr Tyr Asp Ser Ala Asp Leu Asn Gly
385                 390                 395                 400

Gly Asn Leu Gln Thr Gly Leu Thr Ala Gly Gly Glu Ala Leu Thr Ala
            405                 410                 415

Val Ala Asn Gly Lys Thr Thr Asp Pro Leu Lys Ala Leu Asp Asp Ala
            420                 425                 430

Ile Ala Ser Val Asp Lys Phe Arg Ser Ser Leu Gly Ala Val Gln Asn
            435                 440                 445

Arg Leu Asp Ser Ala Val Thr Asn Leu Asn Asn Thr Thr Asn Leu
            450                 455                 460

Ser Glu Ala Gln Ser Arg Ile Gln Asp Ala Asp Tyr Ala Thr Glu Val
465                 470                 475                 480

Ser Asn Met Ser Lys Ala Gln Ile Ile Gln Gln Ala Gly Asn Ser Val
            485                 490                 495

Leu Ala Lys Ala Asn Gln Val Pro Gln Gln Val Leu Ser Leu Leu Gln
            500                 505                 510

Gly
```

<210> SEQ ID NO 19
<211> LENGTH: 513
<212> TYPE: PRT
<213> ORGANISM: Artificial sequence
<220> FEATURE:
<223> OTHER INFORMATION: Synthesized

<400> SEQUENCE: 19

```
Met Ala Gln Val Ile Asn Thr Asn Ser Leu Ser Leu Ile Thr Gln Asn
1               5                   10                  15

Asn Ile Asn Lys Asn Gln Ser Ala Leu Ser Ser Ser Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ala Arg Asn Ala Asn Asp Gly Ile Ser Val Ala Gln Thr Thr Glu Gly
65                  70                  75                  80

Ala Leu Ser Glu Ile Asn Asn Asn Leu Gln Arg Val Arg Glu Leu Thr
                85                  90                  95

Val Gln Ala Thr Thr Gly Thr Asn Ser Glu Ser Asp Leu Ser Ser Ile
            100                 105                 110

Gln Asp Glu Ile Lys Ser Arg Leu Asp Glu Ile Asp Arg Val Ser Gly
        115                 120                 125

Gln Thr Gln Phe Asn Gly Val Asn Val Leu Ala Lys Asn Gly Ser Met
    130                 135                 140

Lys Ile Gln Val Gly Ala Asn Asp Asn Gln Thr Ile Thr Ile Asp Leu
145                 150                 155                 160

Lys Gln Ile Asp Ala Lys Thr Leu Gly Leu Asp Gly Phe Ser Val Lys
                165                 170                 175

Asn Asn Asp Thr Val Thr Thr Ser Ala Pro Val Thr Ala Phe Gly Ala
            180                 185                 190

Thr Thr Thr Asn Asn Ile Lys Leu Thr Gly Ile Thr Leu Ser Thr Glu
        195                 200                 205

Ala Ala Thr Asp Thr Gly Gly Thr Asn Pro Ala Ser Ile Glu Gly Val
    210                 215                 220

Tyr Thr Asp Asn Gly Asn Asp Tyr Tyr Ala Lys Ile Thr Gly Gly Asp
```

-continued

```
            225                 230                 235                 240
Asn Asp Met Ser Asp Lys Ile Ile His Leu Thr Asp Ser Phe Asp
                245                 250                 255
Thr Asp Val Leu Lys Ala Asp Gly Ala Ile Leu Val Asp Phe Trp Ala
                260                 265                 270
Glu Trp Cys Gly Pro Arg Asn Lys Arg Cys Ser Ser Lys Thr Arg Arg
            275                 280                 285
Gly Gly Pro Cys Lys Met Ile Ala Pro Ile Leu Asp Glu Ile Ala Asp
            290                 295                 300
Glu Tyr Gln Gly Lys Leu Thr Val Ala Lys Leu Asn Ile Asp Gln Asn
305                 310                 315                 320
Pro Gly Thr Ala Pro Lys Tyr Gly Ile Arg Gly Ile Pro Thr Leu Leu
                325                 330                 335
Leu Phe Lys Asn Gly Glu Val Ala Ala Thr Lys Val Gly Ala Leu Ser
                340                 345                 350
Lys Gly Gln Leu Lys Glu Phe Leu Asp Ala Asn Leu Ala Cys Ala Ala
                355                 360                 365
Ser Ser Pro Thr Ala Val Lys Leu Gly Gly Asp Asp Gly Lys Thr Glu
    370                 375                 380
Val Val Asp Ile Asp Gly Lys Thr Tyr Asp Ser Ala Asp Leu Asn Gly
385                 390                 395                 400
Gly Asn Leu Gln Thr Gly Leu Thr Ala Gly Gly Glu Ala Leu Thr Ala
                405                 410                 415
Val Ala Asn Gly Lys Thr Thr Asp Pro Leu Lys Ala Leu Asp Asp Ala
                420                 425                 430
Ile Ala Ser Val Asp Lys Phe Arg Ser Ser Leu Gly Ala Val Gln Asn
            435                 440                 445
Arg Leu Asp Ser Ala Val Thr Asn Leu Asn Asn Thr Thr Thr Asn Leu
    450                 455                 460
Ser Glu Ala Gln Ser Arg Ile Gln Asp Ala Asp Tyr Ala Thr Glu Val
465                 470                 475                 480
Ser Asn Met Ser Lys Ala Gln Ile Ile Gln Gln Ala Gly Asn Ser Val
                485                 490                 495
Leu Ala Lys Ala Asn Gln Val Pro Gln Gln Val Leu Ser Leu Leu Gln
                500                 505                 510
Gly
```